United States Patent

Hojo et al.

(10) Patent No.: US 6,380,288 B1
(45) Date of Patent: Apr. 30, 2002

(54) RUBBER COMPOSITION AND PNEUMATIC TIRES

(75) Inventors: Masahiro Hojo; Tomohiro Kusano; Akihiko Matsue; Kenichi Sugimoto; Shigeki Kamo, all of Kodaira; Yoshihisa Tomotaki, Tokushima; Akinori Oka, Tokushima; Ken Hirayama, Tokushima, all of (JP)

(73) Assignees: Bridgestone Corporation, Tokyo; Otsuka Chemical Co., Ltd., Osaka (JP)

( * ) Notice: Subject to any disclaimer, the term of this patent is extended or adjusted under 35 U.S.C. 154(b) by 0 days.

(21) Appl. No.: 09/194,724
(22) PCT Filed: Apr. 2, 1998
(86) PCT No.: PCT/JP98/01530
  § 371 Date: Jul. 17, 2000
  § 102(e) Date: Jul. 17, 2000
(87) PCT Pub. No.: WO98/44040
  PCT Pub. Date: Oct. 8, 1998

(30) Foreign Application Priority Data

| Apr. 2, 1997 | (JP) | 9-084133 |
| Feb. 13, 1998 | (JP) | 10-031751 |
| Feb. 13, 1998 | (JP) | 10-031752 |
| Feb. 13, 1998 | (JP) | 10-031753 |

(51) Int. Cl.[7] ............ C08K 3/04; C08K 5/24; C08K 5/30; C08L 7/00; C08L 9/00
(52) U.S. Cl. ............ 524/191; 524/495; 152/450
(58) Field of Search ............ 524/191, 192, 524/198, 495; 152/450

(56) References Cited

U.S. PATENT DOCUMENTS

| 3,227,552 A | * | 1/1966 | Whitmore | 430/29 |
| 3,755,288 A | * | 8/1973 | Sheppard et al. | 534/816 |
| 4,077,948 A | * | 3/1978 | Cowell et al. | 524/194 |
| 4,124,750 A | | 11/1978 | O'Mahoney, Jr. | |
| 4,211,676 A | * | 7/1980 | Watabe et al. | 521/42 |
| 4,282,052 A | * | 8/1981 | Dobson | 156/79 |
| 5,069,892 A | * | 12/1991 | Nakai | 423/445 |
| 5,155,151 A | * | 10/1992 | Hashimoto et al. | 524/95 |
| 5,470,980 A | * | 11/1995 | Ravichandran et al. | 546/190 |
| 5,534,569 A | * | 7/1996 | Etoh | 524/99 |
| 5,679,744 A | * | 10/1997 | Kawauzra et al. | 525/98 |
| 5,760,114 A | * | 6/1998 | Wideman et al. | 524/254 |
| 5,856,393 A | * | 1/1999 | Matsue et al. | 524/493 |

FOREIGN PATENT DOCUMENTS

| GB | 909753 | 11/1962 |
| GB | 1330393 | 9/1973 |
| JP | 59-78250 | 5/1984 |
| JP | 62215640 | * 9/1987 |
| JP | 62-215640 | 9/1987 |
| JP | 62-220534 | 9/1987 |
| JP | 4-136048 | 5/1992 |
| JP | 7-292157 | 11/1995 |
| JP | 8-175102 | 7/1996 |
| JP | 9-40810 | 2/1997 |
| JP | 10-139934 | 5/1998 |

* cited by examiner

Primary Examiner—Vasu Jagannathan
Assistant Examiner—Callie E. Shasho
(74) Attorney, Agent, or Firm—Sughrue Mion, PLLC

(57) ABSTRACT

A rubber composition prepared by compounding 0.05 to 20 parts by weight of at least one selected from substituted hydrazide compounds represented by the following Formulas (I) to (IV) per 100 parts by weight of a rubber component comprising at least one rubber selected from the group consisting of natural rubber and synthetic rubber, and a pneumatic tire using the same:

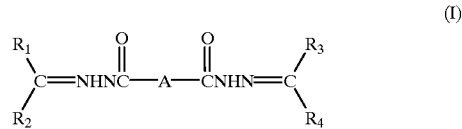

(I)

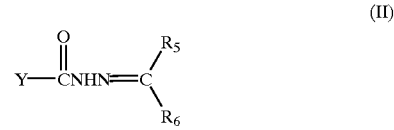

(II)

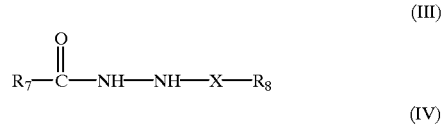

(III)

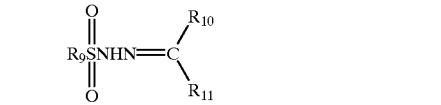

(IV)

wherein A represents one selected from the group consisting of an aromatic group which may have a substituent, a hydantoin ring which may have a substituent, and a saturated or unsaturated linear hydrocarbon having 1 to 18 carbon atoms; Y represents hydrogen, an amino group, an alkyl group having 1 to 18 carbon atoms, a cycloalkyl group, an alkenyl group, an aromatic group, a pyridyl group or hydrazino group; and $R_1$ to $R_{11}$ each represent hydrogen, an alkyl group having 1 to 18 carbon atoms, a cycloalkyl group or an aromatic group.

11 Claims, 1 Drawing Sheet

A: TREAD PART

RUBBER COMPOSITION AND PNEUMATIC TIRES

TECHNICAL FIELD

The present invention relates to a rubber composition providing rubber products which are excellent in aging resistance, and a pneumatic tire.

BACKGROUND ART

In order to prevent aging of rubber products using rubber compositions comprising natural rubber and/or synthetic rubber, various antioxidants have so far been developed.

Further, in order to meet social demands for saving resources and energy in recent years, low heat generation property rubber compositions have actively been developed in the rubber industry.

In general, diphenyldiamine based and hindered phenol based compounds have so far been used as antioxidants. These compounds give H of >NH and —OH to peroxy radicals produced in a process of auto-oxidative degradation to deactivate them, and the compounds themselves turn to stable compounds through more stable radicals. Widely known is such a method that peroxy radicals are deactivated to cut off a radical chain reaction, whereby aging is prevented.

However, both the conventional diphenyldiamine based and hindered phenol based antioxidants described above have an aging-resistant action. In general, the aging-resistant effect increases according as the compounding amount is increased in a range where the compounding amount thereof is small. However, when they are used in large quantities, an increase in the effect gets slow gradually, and the effect is reduced by blooming in a certain case. Accordingly, amount to be used has to be properly restricted.

Further, the diphenyldiamine based antioxidants cause a large change rate of an elastic modulus of rubber before and after degradation of the rubber, and in a certain case, they harden the rubber markedly and deteriorate the rubber properties depending on the ingredients of the rubber composition and the conditions of degradation.

On the other hand, with respect to the aging-resistant characteristics of hydrazide compounds, known are dihydrazide compounds displaying a green strength-improving effect (U.S. Pat. No. 4,124,750), compounds which elevate ozone resistance and in which hydrogen parts of hydrazide and hydrazine are substituted (British Pat. No. 909753) and compounds having an effect as stabilizers for oil extended rubber (British patent 1330393).

Further, it is described in Japanese Pat. No. Publication No. Hei 7-57828 that specific hydrazide compounds can provide a rubber product with a low heat generation property effect and among these compounds, particularly isophthalic dihydrazide (IDH) and 3-hydroxy-2-naphthoic hydrazide can reveal a low heat generation property effect in small amounts.

However, the hydrazide compounds described in these publications, which are compounded into rubber compositions comprising a general sulfur-vulcanizing base rubber, shorten initiation of vulcanization reaction to a large extent and elevate the Mooney viscosity, so that the workability is damaged to a large extent. Accordingly, the compounding amount is restricted only to a small amount, and the satisfactory aging resistant effect is not obtained.

In light of the conventional problems described above, the present invention intends to solve them, and an object thereof is to provide a rubber composition providing rubber products having an excellent aging resistant characteristic and a rubber composition in which workability is not reduced when blended with sulfur vulcanizing agents used extensively in the rubber industry including tire.

Another object of the present invention is to provide a low heat generation property rubber composition which can control an increase in the Mooney viscosity and enhance the workability while maintaining the low heat generation property.

In addition, a further object of the present invention is to provide a pneumatic tire having an excellent aging-resistant characteristic as well as an excellent low heat generation property.

DISCLOSURE OF THE INVENTION

Intensive investigations of the conventional problems described above continued by the present inventors have resulted in newly finding that specific hydrazide compounds obtained as a result of modifying a hydrazide group by various methods so that an influence is not exerted on a vulcanization reaction can achieve the objects described above while maintaining an aging-resistant capability and that some of these compounds have a low heat generation property effect as well, and thus the present invention has come to complete.

That is, the present invention has the following constituents of (1) to (17):

(1) A rubber composition prepared by compounding 0.05 to 20 parts by weight of at least one selected from the group consisting of hydrazide compounds represented by the following Formulas (I) to (IV) per 100 parts by weight of a rubber component comprising at least one rubber selected from the group consisting of natural rubber and synthetic rubber:

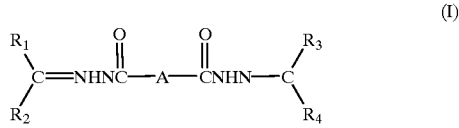

wherein A represents one selected from the group consisting of an aromatic group which may be substituted with at least one substituent containing at least one atom of carbon, sulfur, oxygen and nitrogen atoms, a hydantoin ring which may be substituted with at least one substituent containing at least one atom of carbon, sulfur, oxygen and nitrogen atoms, and a saturated or unsaturated linear hydrocarbon having 1 to 18 carbon atoms; $R_1$ to $R_4$ each represent hydrogen, an alkyl group having 1 to 18 carbon atoms, a cycloalkyl group or an aromatic group which may be substituted with at least one substituent containing at least one atom of carbon, sulfur, oxygen and nitrogen atoms, and each of $R_1$ to $R_4$ may be the same or different, and when $R_1$ and $R_2$ and/or $R_3$ and $R_4$ are alkyl groups, $R_1$ may be bonded to $R_2$ and $R_3$ may be bonded to $R_4$ to form rings;

wherein Y represents hydrogen, an amino group, an alkyl group having 1 to 18 carbon atoms, a cycloalkyl group, an alkenyl group, an aromatic group which may be substituted with at least one substituent containing at least one atom of carbon, sulfur, oxygen and nitrogen atoms, a pyridyl group or hydrazino group, $R_5$ and $R_6$ each represent hydrogen, an alkyl group having 1 to 18 carbon atoms, a cycloalkyl group, an alkenyl group or an aromatic group which may be substituted with at least one substituent containing at least one atom of carbon, sulfur, oxygen and nitrogen atoms, and each of $R_5$ and $R_6$ may be the same or different, and when $R_5$ and $R_6$ are alkyl groups, $R_5$ may be bonded to $R_6$ to form a ring;

(III)

wherein $R_7$ and $R_8$ each represent an alkyl group having 1 to 18 carbon atoms, a cycloalkyl group, an aromatic group which may be substituted with at least one substituent containing at least one atom of carbon, sulfur, oxygen and nitrogen atoms, an alkenyl group, an amino group or an alkylamino group and each of $R_7$ and $R_8$ may be the same or different; and X represents a single bond or any of the groups represented by the following formulas;

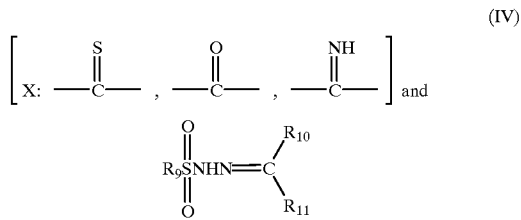

(IV)

wherein $R_9$ represents hydrogen, an alkoxy group, an amino group, a substituted amino group, an alkyl group having 1 to 18 carbon atoms, a cycloalkyl group, an alkenyl group or an aromatic group which may be substituted with at least one substituent containing at least one atom of carbon, sulfur, oxygen and nitrogen atoms; and $R_{10}$ and $R_{11}$ each represent hydrogen, an alkyl group having 1 to 18 carbon atoms, a cycloalkyl group, an alkenyl group or an aromatic group which may be substituted with at least one substituent containing at least one atom of carbon, sulfur, oxygen and nitrogen atoms, and each of $R_{10}$ and $R_{11}$ may be the same or different, and when $R_{10}$ and $R_{11}$ are alkyl groups, $R_{10}$ may be bonded to $R_{11}$ to form a ring.

(2) The rubber composition as described in the above item (1), containing 30 phr or more of natural rubber (which may be polyisoprene rubber) as the rubber component.

(3) The rubber composition as described in the above item (1) or (2), prepared by further compounding 20 to 150 parts by weight of a reinforcing filler.

(4) The rubber composition as described in the above item (3), wherein the reinforcing filler is carbon black.

(5) The rubber composition as described in any of the above items (1) to (4), wherein A in Formula (I), Y in Formula (II), $R_7$ in Formula (III) and $R_9$ in Formula (IV) in the hydrazide compounds represented by Formulas (I) to (IV) described above represent a phenyl group (may be substituted with at least one substituent containing at least one atom of carbon, sulfur, oxygen and nitrogen atoms) or a naphthyl group (may be substituted with at least one substituent containing at least one atom of carbon, sulfur, oxygen and nitrogen atoms).

(6) The rubber composition as described in the above item (5), wherein the compound represented by Formula (I) described above is $N^2,N^4$-di(1-methylethylidene)isophthalodihydrazide, $N^2,N^4$-di(1-methylpropylidene)isophthalodihydrazide or $N^2,N^4$-di(1,3-dimethylbutylidene)isophthalodihydrazide.

(7) The rubber composition as described in the above item (5), wherein the hydrazide compound represented by Formula (II) described above is N'-(1-methylethylidene)salicylohydrazide, N'-(1-methylpropylidene)salicylohydrazide, N'-(1,3-dimethylbutylidene)salicylohydrazide, N'-(2-furylmethylene)salicylohydrazide, 1-hydroxy-N'-(1-methylethylidene)-2-naphthohydrazide, 1-hydroxy-N'-(1-methylpropylidene)-2-naphthohydrazide, 1-hydroxy-N'-(1,3-dimethylbutylidene)-2-naphthohydrazide, 1-hydroxy-N'-(2-furylmethylene)-2-naphthohydrazide, 3-hydroxy-N'-(1-methylethylidene)-2-naphthohydrazide, 3-hydroxy-N'-(1-methylpropylidene)-2-naphthohydrazide, 3-hydroxy-N'-(1,3-dimethylbutylidene)-2-naphthohydrazide or 3-hydroxy-N'-(2-furylmethylene)-2-naphthohydrazide.

(8) The rubber composition as described in the above item (5), wherein the hydrazide compound represented by Formula (III) described above is N-benzoyl-N'-phenylhydrazide, 1-benzamidoguanidine or 1-benzoylsemicarbazide.

(9) The rubber composition as described in the above item (5), wherein the hydrazide compound represented by Formula (IV) described above is N'-(1-methylethylidene)benzenesulfonohydrazide, N'-(1-methylpropylidene)benzenesulfonohydrazide, N'-(1,3-dimethylbutylidene)benzenesulfonohydrazide, N'-(1-phenylethylidene)benzenesulfonohydrazide, N'-(2-hydroxybenzylidene)benzenesulfonohydrazide, N'-diphenylmethylenebenzenesulfonohydrazide, N'-(2-furylmethylene)benzenesulfonohydrazide, N'-(1-methylethylidene)-p-toluenesulfonohydrazide, N'-(1-methylpropylidene)-p-toluenesulfonohydrazide, N'-(1,3-dimethylbutylidene)-p-toluenesulfonohydrazide, N'-benzylidene-p-toluenesulfonohydrazide, N'-(1-phenylethylidene)-p-toluenesulfonohydrazide, N'-(2-hydroxybenzylidene)-p-toluenesulfonohydrazide, N'-diphenylmethylene-p-toluenesulfonohydrazide or N'-(2-furylmethylene)-p-toluenesulfonohydrazide.

(10) The rubber composition as described in any of the above items (1) to (9), prepared by further compounding 0.1 to 5.0 parts by weight of at least one selected from antioxidants of naphthylamine base, p-phenylenediamine base, hydroquinone derivative, bisphenol base, trisphenol base, polyphenol base, diphenylamine base, quinoline base, monophenol base, thiobisphenol base and hindered phenol base.

(11) A pneumatic tire characterized by using a rubber composition prepared by compounding 0.05 to 5 parts by weight of at least one selected from the group consisting of the hydrazide compounds represented by Formulas (I) to (IV) described above per 100 parts by weight of a rubber component comprising natural rubber and diene based rubber as principal components.

(12) The pneumatic tire as described in the above item (11), wherein the rubber composition prepared by compounding 0.05 to 5 parts by weight of at least one selected from the group consisting of the hydrazide compounds represented by Formulas (I) to (IV) described above per 100 parts by weight of the rubber component comprising natural rubber and diene based rubber as principal components is used for a tire tread part.

(13) The pneumatic tire as described in the above item (12), wherein the rubber composition prepared by compounding 0.05 to 5 parts by weight of at least one selected from the group consisting of the hydrazide compounds represented by Formula (II) described above per 100 parts by weight of the rubber component comprising natural rubber and diene based rubber as principal components is used for a tire tread part.

(14) The pneumatic tire as described in the above item (13), wherein the hydrazide compound represented by Formula (II) described above is N'-(1-methylethylidene)salicylohydrazide, N'-(1-methylpropylidene)salicylohydrazide, N'-(1,3-dimethylbutylidene)salicylohydrazide, N'-(2-furylmethylene)salicylohydrazide, 1-hydroxy-N'-(1-methylethylidene)-2-naphthohydrazide, 1-hydroxy-N'-(1-methylpropylidene)-2-naphthohydrazide, 1-hydroxy-N'-(1,3-dimethylbutylidene)-2-naphthohydrazide, 1-hydroxy-N'-(2-furylmethylene)-2-naphthohydrazide, 3-hydroxy-N'-(1-methylethylidene)-2-naphthohydrazide, 3-hydroxy-N'-(1-methylpropylidene)-2-naphthohydrazide, 3-hydroxy-N'-(1,3-dimethylbutylidene)-2-naphthohydrazide or 3-hydroxy-N'-(2-furylmethylene)-2-naphthohydrazide.

(15) The pneumatic tire as described in the above item (12), wherein 30 to 70 parts by weight of carbon black having a specific surface area by nitrogen adsorption ($N_2SA$) of 30 to 180 $m^2/g$ and a dibutyl phthalate absorption (DBP) of 60 to 200 ml/100 g is compounded per 100 parts by weight of the rubber component comprising natural rubber and diene based rubber as principal components; and the hydrazide compound is one in which A in Formula (I) described above is an aromatic group.

(16) The pneumatic tire as described in the above item (13), wherein 30 to 70 parts by weight of carbon black having a specific surface area by nitrogen adsorption ($N_2SA$) of 30 to 180 $m^2/g$ and a dibutyl phthalate absorption (DBP) of 60 to 200 ml/100 g is compounded per 100 parts by weight of the rubber component comprising natural rubber and diene based rubber as principal components; and Y in Formula (II) described above is an aromatic group substituted with a hydroxyl group or an amino group.

(17) A hydrazone derivative represented by Formula (V):

ZC(=O)NHN=C(CH$_3$)(CH$_2$CH(CH$_3$)$_2$)    (V)

wherein Z represents 3-hydroxy-2-naphthyl, 1-hydroxy-2-naphthyl, 2-hydroxyphenyl or 2,6-dihydroxyphenyl group.

BEST MODE FOR CARRYING OUT THE INVENTION

Figure 1:
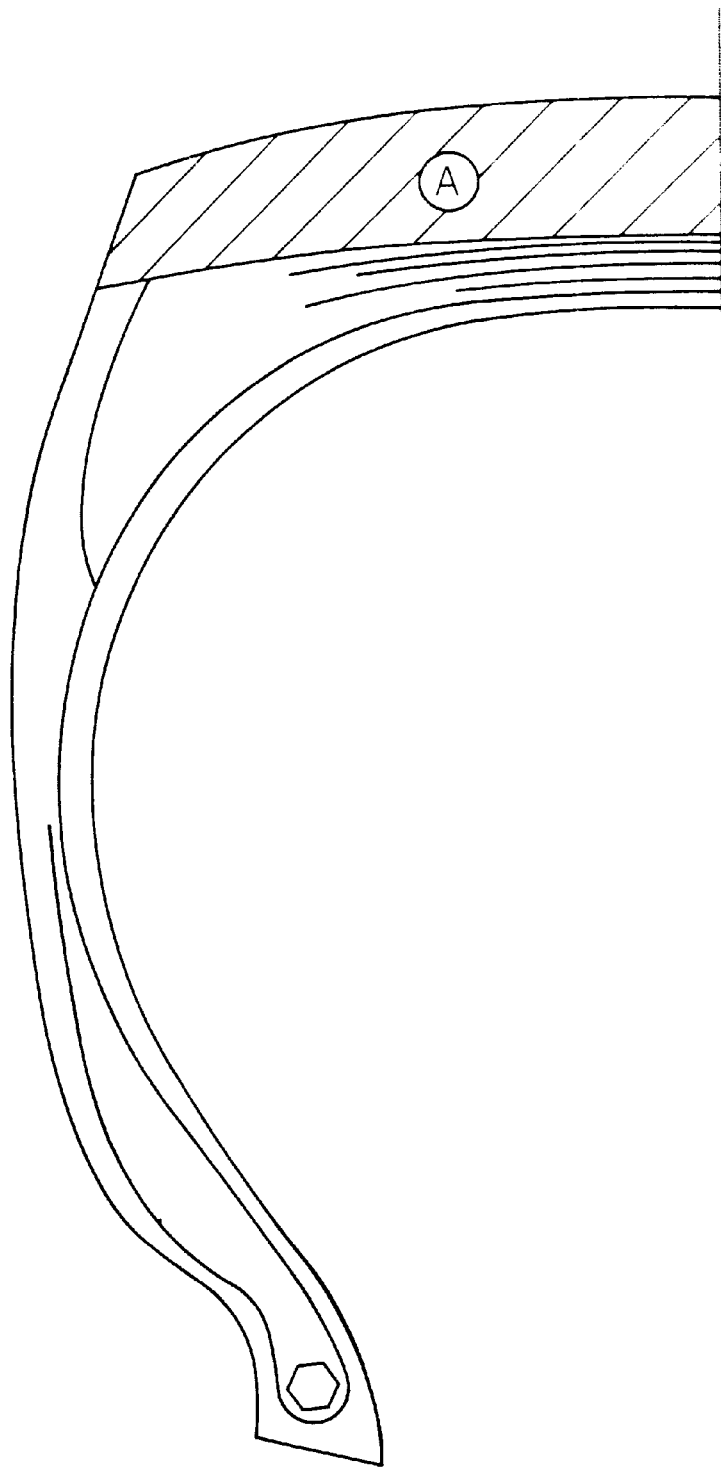
FIG. 1 shows a partial longitudinal cross section showing one example of a pneumatic tire, and A shows a tread part which is the characteristic of the present invention.

A mode for carrying out the present invention shall be explained below in detail.

The rubber composition of the present invention is prepared by compounding 0.05 to 20 parts by weight of at least one selected from the group consisting of hydrazide compounds represented by the following Formulas (I) to (IV) per 100 parts by weight of a rubber component comprising at least one rubber selected from the group consisting of natural rubber and synthetic rubber:

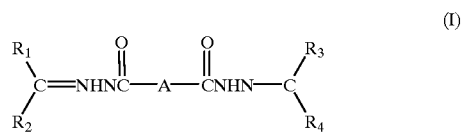
(I)

wherein A represents one selected from the group consisting of an aromatic group which may be substituted with at least one substituent containing at least one atom of carbon, sulfur, oxygen and nitrogen atoms, a hydantoin ring which may be substituted with at least one substituent containing at least one atom of carbon, sulfur, oxygen and nitrogen atoms, and a saturated or unsaturated linear hydrocarbon having 1 to 18 carbon atoms; $R_1$ to $R_4$ each represent hydrogen, an alkyl group having 1 to 18 carbon atoms, a cycloalkyl group or an aromatic group which may be substituted with at least one substituent containing at least one atom of carbon, sulfur, oxygen and nitrogen atoms, and each of $R_1$ to $R_4$ may be the same or different, and when $R_1$ and $R_2$ and/or $R_3$ and $R_4$ are alkyl groups, $R_1$ may be bonded to $R_2$ and $R_3$ may be bonded to $R_4$ to form rings;

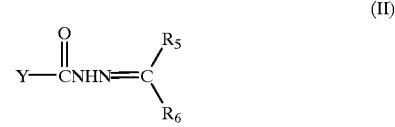
(II)

wherein Y represents hydrogen, an amino group, an alkyl group having 1 to 18 carbon atoms, a cycloalkyl group, an alkenyl group, an aromatic group which may be substituted with at least one substituent containing at least one atom of carbon, sulfur, oxygen and nitrogen atoms, a pyridyl group or hydrazino group; $R_5$ and $R_6$ each represent hydrogen, an alkyl group having 1 to 18 carbon atoms, a cycloalkyl group, an alkenyl group or an aromatic group which may be substituted with at least one substituent containing at least one atom of carbon, sulfur, oxygen and nitrogen atoms, and each of $R_5$ and $R_6$ may be the same or different, and when $R_5$ and $R_6$ are alkyl groups, $R_5$ may be bonded to $R_6$ to form a ring;

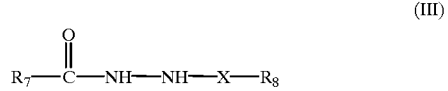
(III)

wherein $R_7$ and $R_8$ each represent an alkyl group having 1 to 18 carbon atoms, a cycloalkyl group, an aromatic group which may be substituted with at least one substituent containing at least one atom of carbon, sulfur, oxygen and nitrogen atoms, an alkenyl group, an amino group or an alkylamino group and each of $R_7$ and $R_8$ may be the same or different; and X represents a single bond or any of the groups represented by the following groups;

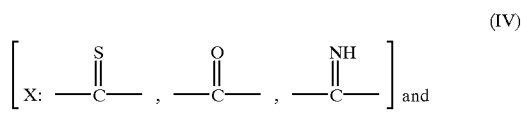
(IV)

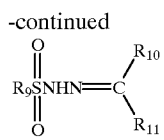

wherein $R_9$ represents hydrogen, an alkoxy group, an amino group, a substituted amino group, an alkyl group having 1 to 18 carbon atoms, a cycloalkyl group, an alkenyl group or an aromatic group which may be substituted with at least one substituent containing at least one atom of carbon, sulfur, oxygen and nitrogen atoms; and $R_{10}$ and $R_{11}$ each represent hydrogen, an alkyl group having 1 to 18 carbon atoms, a cycloalkyl group, an alkenyl group or an aromatic group which may be substituted with at least one substituent containing at least one atom of carbon, sulfur, oxygen and nitrogen atoms, and each of $R_{10}$ and $R_{11}$ may be the same or different, and when $R_{10}$ and $R_{11}$ are alkyl groups, $R_{10}$ may be bonded to $R_{11}$ to form a ring.

With respect to a mechanism of an aging-resistant action of a hydrazide compound, it is considered that >NH contained in the structure of the hydrazide compound as is the case with conventional diphenyldiamine based antioxidants provides peroxy radicals produced in an auto-oxidation process of rubber with protons to stabilize, whereby an aging-resistant action is shown.

The hydrazide compounds used in the present invention consisting of the compound groups represented by Formulas (I) to (IV) described above are prepared by modifying a hydrazide group, which accelerates vulcanization reaction, with ketone, aldehyde and sulfonic acid, and it is presumed that these modified hydrazide compounds restrain reaction of rubber with a vulcanization-accelerating agent and sulfur while maintaining an effect as an antioxidant, so that the aging-resistant effect can be compatible with the workability (this matter shall be explained in further detail with reference to examples described later).

Further, among the compounds used in the present invention represented by Formulas (I) and (II) described above, the hydrazide compounds in which respective A and Y are an aromatic group having substituents have an action to control an increase in the viscosity as well as an aging-resistant effect while maintaining a low heat generation property effect of rubber. The action mechanism thereof resides in reducing the reactivity of the hydrazide group with a rubber polymer by modifying the hydrazide group as mentioned above. In addition, the hydrazide compounds have a function to maintain and enhance the reactivity of rubber with carbon black.

A of the compound (I) used in the present invention includes an aromatic group which may be substituted with at least one substituent containing at least one atom of carbon, sulfur, oxygen and nitrogen atoms, a hydantoin ring which may be substituted with at least one substituent containing at least one atom of carbon, sulfur, oxygen and nitrogen atoms, and a saturated or unsaturated linear hydrocarbon having 1 to 18 carbon atoms such as ethylene, tetramethylene, heptamethylene, octamethylene, octadecamethylene and 7,11-octadecadienylene group.

Further, $R_1$ to $R_4$ each represent hydrogen, an alkyl group having 1 to 18 carbon atoms, a cycloalkyl group or an aromatic group which may be substituted with at least one substituent containing at least one atom of carbon, sulfur, oxygen and nitrogen atoms, and each of $R_1$ to $R_4$ may be the same or different, and when $R_1$ and $R_2$ and/or $R_3$ and $R_4$ are alkyl groups, $R_1$ may be bonded to $R_2$ and $R_3$ may be bonded to $R_4$ to form rings.

The specific compounds represented by Formula (I) described above include $N^2,N^4$-di(1-methylethylidene) isophthalodihydrazide, $N^2,N^4$-di(1-methylethylidene) adipodihydrazide, $N^2,N^4$-di(1-methylpropylidene) isophthalodihydrazide, $N^2,N^4$-di(1-methylpropylidene) adipodihydrazide, $N^2,N^4$-di(1-methylbutylidene) isophthalodihydrazide, $N^2,N^4$-di(1-methylbutylidene) adipodihydrazide, $N^2,N^4$-di(1,3-dimethylbutylidene) isophthalodihydrazide, $N^2, N^4$-di(1,3-dimethylbutylidene) adipodihydrazide, $N^2,N^4$-di(1-phenylethylidene) isophthalodihydrazide and $N^2,N^4$-di(1-phenylethylidene) adipodihydrazide, which are the derivatives of isophthalodihydrazide and adipodihydrazide. In addition to these derivatives of isophthalodihydrazide and adipodihydrazide, the derivatives of the following dihydrazide compounds provide the similar effect.

They include, for example, the derivatives of terephthalodihydrazide, azelaodihydrazide, succinodihydrazide and icosanodicarboxylic dihydrazide.

Among them, the derivatives of isophthalodihydrazide such as $N^2,N^4$-di(1-methylethylidene) isophthalodihydrazide, $N^2,N^4$-di(1-methylpropylidene) isophthalodihydrazide and $N^2,N^4$-di(1,3-dimethylbutylidene)isophthalodihydrazide which provide an aging-resistant effect and a good low heat generation property effect and markedly inhibit an increase in the Mooney viscosity value provide the largest effect with respect to the present invention and can reduce the Mooney viscosity while maintaining the low heat generation property.

Specific hydrazide compounds used in the present invention consisting of the compound group represented by Formula (II) described above include the following compounds.

The compounds in which Y is an aromatic group include:

N'-(1-methylethylidene)benzohydrazide,
N'-(1-methylpropylidene)benzohydrazide,
N'-(1,3-dimethylbutylidene)benzohydrazide,
N'-benzylidenebenzohydrazide,
N'-(4-dimethylaminobenzylidene)benzohydrazide,
N'-(4-methoxybenzylidene)benzohydrazide,
N'-(2-hydroxybenzylidene)benzohydrazide,
N'-(4-hydroxybenzylidene)benzohydrazide,
N'-diphenylethylidenebenzohydrazide,
N'-(1-phenylmethylene)benzohydrazide,
N'-(α-(2,4-dihydroxyphenyl)benzylidene) benzohydrazide,
N'-(2-furylmethylene)benzohydrazide,
N'-(1-methylethylidene)salicylohydrazide,
N'-(1-methylpropylidene)salicylohydrazide,
N'-(1-methylbutylidene)salicylohydrazide,
N'-(1,3-dimethylbutylidene)salicylohydrazide,
N'-(2-furylmethylene)salicylohydrazide,
2,6-dihydroxy-N'-(1,3-dimethylbutylidene) benzohydrazide,
N'-(1-methylethylidene)-1-naphthohydrazide,
N'-(1-methylpropylidene)-1-naphthohydrazide,
N'-(1,3-dimethylbutylidene)-1-naphthohydrazide,
N'-benzylidene-1-naphthohydrazide,
N'-(4-dimethylaminobenzylidene)-1-naphthohydrazide,
N'-(4-methoxybenzylidene)-1-naphthohydrazide,
N'-(4-hydroxybenzylidene)-1-naphthohydrazide, N'-(1-phenylethylidene)-1-naphthohydrazide,
N'-diphenylmethylene-1-naphthohydrazide,
N'-(α-(2,4-dihydroxyphenyl)benzylidene)-1-naphthohydrazide,
N'-(2-furylmethylene)-1-naphthohydrazide,
N'-(1-methylethylidene)-2-naphthohydrazide,
N'-(1-methylpropylidene)-2-naphthohydrazide,
N'-(1,3-dimethylbutylidene)-2-naphthohydrazide,
N'-benzylidene-2-naphthohydrazide,
N'-(4-dimethylaminobenzylidene)-2-naphthohydrazide,
N'-(4-methoxybenzylidene)-2-naphthohydrazide,
N'-(2-hydroxybenzylidene)-2-naphthohydrazide,
N'-(4-hydroxybenzylidene)-2-naphthohydrazide,
N'-(1-phenylethylidene)-2-naphthohydrazide,
N'-diphenylmethylene-2-naphthohydrazide,
N'-(α-(2,4-dihydroxyphenyl)benzylidene)-2-naphthohydrazide,
1-hydroxy-N'-(1-methylethylidene)-2-naphthohydrazide,
1-hydroxy-N'-(1-methylpropylidene)-2-naphthohydrazide,
1-hydroxy-N'-(1-methylbutylidene)-2-naphthohydrazide,
1-hydroxy-N'-(1,3-dimethylbutylidene)-2-naphthohydrazide,
1-hydroxy-N'-(2-furylmethylene)-2-naphthohydrazide,
3-hydroxy-N'-(1-methylethylidene)-2-naphthohydrazide,
3-hydroxy-N'-(1-methylpropylidene)-2-naphthohydrazide,
3-hydroxy-N'-(1-methylbutylidene)-2-naphthohydrazide,
3-hydroxy-N'-(1,3-dimethylbutylidene)-2-naphthohydrazide,
3-hydroxy-N'-(1-phenylethylidene)-2-naphthohydrazide, and
3-hydroxy-N'-(2-furylmethylene)-2-naphthohydrazide, as well as 4-hydroxybenzohydrazide and anthranilohydrazide. These N'-(1,3-dimethylbutylidene) salicylohydrazide, 1-hydroxy-N'-(1,3-dimethylbutylidene)-2-naphthohydrazide, 2,6-dihydroxy-N'-(1,3-dimethylbutylidene)benzohydrazide and 3-hydroxy-N'-(1,3-dimethylbutylidene)-2-naphthohydrazide are novel substances.

The compounds in which Y is an alkyl group include:
N'-(1-methylethylidene)propionohydrazide,
N'-(1-methylpropylidene)propionohydrazide,
N'-(1,3-dimethylbutylidene)propionohydrazide,
N'-benzylidenepropionohydrazide,
N'-(4-dimethylaminobenzylidene)propionohydrazide,
N'-(4-methoxybenzylidene)propionohydrazide,
N'-(2-hydroxybenzylidene) propionohydrazide,
N'-(4-hydroxybenzylidene)propionohydrazide,
N'-(1-phenylethylidene)propionohydrazide,
N'-diphenylmethylenepropionohydrazide,
N'-(α-(24-dihydroxyphenyl)benzylidene)propionohydrazide,
N'-(2-furylmethylene)propionohydrazide,
N'-(1-methylethylidene)-2-methylpropionohydrazide,
N'-(1-methylpropylidene)-2-methylpropionohydrazide,
N'-(1,3-dimethylbutylidene)-2-methylpropionohydrazide,
N'-benzylidene-2-methylpropionohydrazide,
N'-(4-dimethylaminobenzylidene)-2-methylpropionohydrazide,
N'-(4-methoxybenzylidene)-2-methylpropionohydrazide,
N'-(4-hydroxybenzylidene)-2-methylpropionohydrazide,
N'-(1-phenylethylidene)-2-methylpropionohydrazide,
N'-diphenylmethylene-2-methylpropionohydrazide,
N'-(α-(2,4-dihydroxyphenyl)benzylidene)-2-methylpropionohydrazide,
N'-(2-furylmethylene)-2-methylpropionohydrazide,
N'-(1-methylethylidene)-2,2'-dimethylpropionohydrazide,
N'-(1-methylpropylidene)-2,2'-dimethylpropionohydrazide,
N'-(1,3-dimethylbutylidene)-2,2'-dimethylpropionohydrazide,
N'-benzylidene-2,2'-dimethylpropionohydrazide,
N'-(4-dimethylaminobenzylidene)-2,2'-dimethylpropionohydrazide,
N'-(4-methoxybenzylidene)-2,2'-dimethylpropionohydrazide,
N'-(4-hydroxybenzylidene)-2,2'-dimethylpropionohydrazide,
N'-(1-phenylethylidene)-2,2'-dimethylpropionohydrazide,
N'-diphenylmethylene-2,2'-dimethylpropionohydrazide,
N'-(α-(2,4-dihydroxyphenyl)benzylidene)-2,2'-dimethylpropionohydrazide,
N'-(2-furylmethylene)-2,2'-dimethylpropionohydrazide,
N'-(1-methylethylidene)octanohydrazide,
N'-(1-methylpropylidene)octanohydrazide,
N'-(1,3-dimethylbutylidene)octanohydrazide,
N'-benzylideneoctanohydrazide,
N'-(4-dimethylaminobenzylidene)octanohydrazide,
N'-(4-methoxybenzylidene)octanohydrazide,
N'-(4-hydroxybenzylidene)octanohydrazide,
N'-(1-phenylethylidene)octanohydrazide,
N'-diphenylmethyleneoctanohydrazide,
N'-(α-(2,4-dihydroxyphenyl)benzylidene)octanohydrazide,
N'-(2-furylmethylene)octanohydrazide,
N'-(1-methylethylidene)stearohydrazide,
N'-(1-methylpropylidene)stearohydrazide,
N'-(1,3-dimethylbutylidene)stearohydrazide,
N'-benzylidenestearohydrazide,
N'-(4-dimethylaminobenzylidene)stearohydrazide,
N'-(4-methoxybenzylidene)stearohydrazide,
N'-(2-hydroxybenzylidene)stearohydrazide,
N'-(4-hydroxybenzylidene)stearohydrazide,
N'-(1-phenylethylidene)stearohydrazide,
N'-diphenylmethylenestearohydrazide,
N'-(α-(2,4-dihydroxyphenyl)benzylidene)stearohydrazide,
N'-(2-furylmethylene)stearohydrazide.

The compounds in which Y is a pyridyl group or a hydrazino group include the derivatives of isonicotiniohydrazide such as N'-(1-methylethylidene)isonicotinohydrazide, N'-(1-methylpropylidene)isonicotinohydrazide, N'-(1,3-dimethylbutylidene)

isonicotinohydrazide and N'-(1-phenylethylidene) isonicotinohydrazide, as well as the derivatives of carbohydrazide.

Among these hydrazide compounds, the following compounds are preferred since they have an aging-resistant effect as well as a low heat generation property:

N'-(1-methylethylidene)salicylohydrazide

N'-(1-methylpropylidene)salicylohydrazide,

N'-(1,3-dimethylbutylidene)salicylohydrazide,

N'-(2-furylmethylene)salicylohydrazide, 1-hydroxy-N'-(1-methylethylidene)-2-naphthohydrazide, 1-hydroxy-N'-(1-methylpropylidene)-2-naphthohydrazide, 1-hydroxy-N'-(1,3-dimethylbutylidene)-2-naphthohydrazide, 3-hydroxy-N'-(2-furylmethylene)-2-naphthohydrazide, 3-hydroxy-N'-(1-methylethylidene)-2-naphthohydrazide, 3-hydroxy-N'-(1-methylpropylidene)-2-naphthohydrazide, 3-hydroxy-N'-(1,3-dimethylbutylidene)-2-naphthohydrazide and 3-hydroxy-N'-(2-furylmethylene)-2-naphthohydrazide, Synthetic methods of the hydrazide compounds represented by Formulas (I) and (II) described above are described in the literature : Pant, U. C.; Ramchandran, Reena; Joshi, B. C., Rev. Roum. Chim. (1979) 24 (3), 471–82, and they can easily be synthesized by reacting compounds having hydrazide with prescribed aldehyde and ketone. The specific synthetic examples shall further be explained in the section of the examples.

The hydrazide compounds represented by Formula (III) described above include, for example, N-benzoyl-N'-methylhydrazine, N-benzoyl-N'-ethylhydrazine, N-benzoyl-N'-n-butylhydrazine, N-benzoyl-N'-isobutylhydrazine, N-benzoyl-N'-t-butylhydrazine, N-benzoyl-N'-stearylhydrazine, N-benzoyl-N'-cyclohexylhydrazine, N-benzoyl-N'-phenylhydrazine, N-benzoyl-N'-α-naphthylhydrazine, N-benzoyl-N'-β-naphthylhydrazine, N-ethyl-N'-salicyloylhydrazine, N-n-butyl-N'-salicyloylhydrazine, N-isobutyl-N'-α-salicyloylhydrazine, N-t-butyl-N'-salicyloylhydrazine, N-stearyl-N'-salicyloylhydrazine, N-cyclohexyl-N'-salicyloylhydrazine, N-phenyl-N'-salicyloylhydrazine, N-α-naphthyl-N'-salicyloylhydrazine, N-β-naphthyl-N'-salicyloylhydrazine, N-ethyl-N'-α-naphthoylhydrazine, N-n-butyl-N'-α-naphthoylhydrazine, N-isobutyl-N'-α-naphthoylhydrazine, N-t-butyl-N'-α-naphthoylhydrazine, N-stearyl-N'-α-naphthoylhydrazine, N-cyclohexyl-N'-α-naphthoylhydrazine, N-phenyl-N'-α-naphthoylhydrazine, N-α-naphthoyl-N'-α-naphthoylhydrazine, N-α-naphthoyl-N'-β-naphthoylhydrazine, N-ethyl-N'-β-naphthoylhydrazine, N-n-butyl-N'-β-naphthoylhydrazine, N-isobutyl-N'-naphthoylhydrazine, N-t-butyl-N'-β-naphthoylhydrazine, N-stearyl-N'-β-naphthoylhydrazine, N-cyclohexyl-N'-β-naphthoylhydrazine, N-phenyl-N'-β-naphthoylhydrazine, N-a -naphthyl-N'-β-naphthoylhydrazine, N-β-naphthyl-N'-β-naphthoylhydrazine, N-ethyl-N'-valerylhydrazine, N-n-butyl-N'-valerylhydrazine, N-isobutyl-N'-valerylhydrazine, N-t-butyl-N'-valerylhydrazine, N-stearyl-N'-valerylhydrazine, N-cyclohexyl-N'-valerylhydrazine, N-phenyl-N'-valerylhydrazine, N-α-naphthyl-N'-valerylhydrazine, N-β-naphthyl-N'-valerylhydrazine, N-ethyl-N'-isovalerylhydrazine, N-n-butyl-N'-isovalerylhydrazine, N-isobutyl-N'-isovalerylhydrazine, N-t-butyl-N'-isovalerylhydrazine, N-isovaleryl-N'-stearylhydrazine, N-cyclohexyl-N'-isovalerylhydrazine, N-isovaleryl-N'-phenylhydrazine, N-isovaleryl-N'-α-naphthylhydrazine, N-isovaleryl-N'-β-naphthylhydrazine, N-ethyl-N'-pivaloylhydrazine, N-n-butyl-N'-pivaloylhydrazine, N-isobutyl-N'-pivaloylhydrazine, N-t-butyl-N'-pivaloylhydrazine, N-stearyl-N'-pivaloylhydrazine, N-cyclohexyl-N'-pivaloylhydrazine, N-phenyl-N'-pivaloylhydrazine, N-α-naphthyl-N'-pivaloylhydrazine, N-β-naphthyl-N'-pivaloylhydrazine, N-ethyl-N'-stearoylhydrazine, N-n-butyl-N'-stearoylhydrazine, N-isobutyl-N'-stearoylhydrazine, N-t-butyl-N'-stearoylhydrazine, N-stearyl-N'-stearoylhydrazine, N-cyclohexyl-N'-stearoylhydrazine, N-phenyl-N'-stearoylhydrazine, N-α-naphthyl-N'-stearoylhydrazine, N-β-naphthyl-N'-stearoylhydrazine, N-benzoyl-N'-butyrylhydrazine, N-benzoyl-N'-pivaloylhydrazine, N-benzoyl-N'-stearoylhydrazine, N-benzoyl-N'-α-naphthoylhydrazine, N-benzoyl-N'-β-naphthoylhydrazine, N-benzoyl-N'-salicyloylhydrazine, N,N'-dibenzoylhydrazine, 1-benzoylsemicarbazide, N-butyryl-N'-salicyloylhydrazine, N-pivaloyl-N'-salicyloylhydrazine, N-salicyloyl-N'-stearoylhydrazine, N-α-naphthoyl-N'-salicyloylhydrazine, N-β-naphthoyl-N'-salicyloylhydrazine, N,N'-disalicyloylhydrazine, 1-salicyloylsemicarbazide, N-butyryl-N'-α-naphthoylhydrazine, N-α-naphthoyl-N'-pivaloylhydrazine, N-α-naphthoyl-N'-stearoylhydrazine, N-butyryl-N'-β-naphthoylhydrazine, N-β-naphthoyl-N'-pivaloylhydrazine, N-β-naphthoyl-N'-stearoylhydrazine, N,N'-dibutyrylhydrazine, N,N'-dipivaloylhydrazine, 1-benzamidoguanidine and 1-benzoylthiosemicarbazide.

In the hydrazide compound represented by Formula (III) described above used in the present invention, $R_7$ in Formula (III) is preferably phenyl or naphthyl, and to be specific, the hydrazide compound is preferably N-benzoyl-N'-phenylhydrazine, 1-benzamidoguanidine or 1-benzoylsemicarbazide. In these cases, further excellent aging-resistant action shall be displayed.

These hydrazide compounds can readily be synthesized by reacting various hydrazide compounds with benzoyl chloride and the like in the presence of sodium acetate in an acetic acid solution. The specific synthetic methods thereof shall further be explained in the section of the examples.

The sulfonohydrazide compounds represented by Formula (IV) used in the present invention include the following compounds:

N'-(1-methylethylidene)benzenesulfonohydrazide,

N'-(1-methylpropylidene)benzenesulfonohydrazide,

N'-(1,3-dimethylbutylidene)benzenesulfonohydrazide,

N'-benzylidenebenzenesulfonohydrazide,

N'-(4-dimethylaminobenzylidene)benzenesulfonohydrazide,

N'-(4-methoxybenzylidene)benzenesulfonohydrazide,

N'-(2-hydroxybenzylidene)benzenesulfonohydrazide,

N'-(4-hydroxybenzylidene)benzenesulfonohydrazide,

N'-(1-phenylethylidene)benzenesulfonohydrazide,

N'-diphenylmethylenebenzenesulfonohydrazide,

N'-(α-(2,4-dihydroxyphenyl)benzylidene)benzenesulfonohydrazide,

N'-(2-furylmethylene)benzenesulfonohydrazide,

N'-(1-methylethylidene)-p-toluenesulfonohydrazide,

N'-(1-methylpropylidene)-p-toluenesulfonohydrazide,

N'-(1,3-dimethylbutylidene)-p-toluenesulfonohydrazide,

N'-benzylidene-p-toluenesulfonohydrazide,

N'-(4-dimethylaminobenzylidene)-p-toluenesulfonohydrazide,
N'-(4-methoxybenzylidene)-p-toluenesulfonohydrazide,
N'-(2-hydroxybenzylidene)-p-toluenesulfonohydrazide,
N'-(4-hydroxybenzylidene)-p-toluenesulfonohydrazide,
N'-(1-phenylethylidene)-p-toluenesulfonohydrazide,
N'-diphenylmethylene-p-toluenesulfonohydrazide,
N'-(α-(2,4-dihydroxyphenyl)benzylidene)-p-toluenesulfonohydrazide,
N'-(2-furylmethylene)-p-toluenesulfonohydrazide,
N'-(1-methylethylidene)-1-naphthalenesulfonohydrazide,
N'-(1-methylpropylidene)-1-naphthalenesulfonohydrazide,
N'-(1,3-dimethylbutyidene)-1-naphthalenesulfonohydrazide,
N'-benzylidene-1-naphthalenesulfonohydrazide,
N'-(4-dimethylaminobenzylidene)-1-naphthalenesulfonohydrazide,
N'-(4-methoxybenzylidene)-1-naphthalenesulfonohydrazide,
N'-(2-hydroxybenzylidene)-1-naphthalenesulfonohydrazide,
N'-(4-hydroxybenzylidene)-1-naphthalenesulfonohydrazide,
N'-(1-phenylethylidene)-1-naphthalenesulfonohydrazide,
N'-diphenylmethylene-1-naphthalenesulfonohydrazide,
N'-(α-(2,4-dihydroxyphenyl)benzylidene)-1-naphthalenesulfonohydrazide,
N'-(2-furylmethylene)-1-naphthalenesulfonohydrazide,
N'-(1-methylethylidene)-2-naphthalenesulfonohydrazide,
N'-(1-methylpropylidene)-2-naphthalenesulfonohydrazide,
N'-(1,3-dimethylbutyidene)-2-naphthalenesulfonohydrazide,
N'-benzylidene-2-naphthalenesulfonohydrazide,
N'-(4-dimethylaminobenzylidene)-2-naphthalenesulfonohydrazide,
N'-(4-methoxybenzylidene)-2-naphthalenesulfonohydrazide,
N'-(2-hydroxybenzylidene)-2-naphthalenesulfonohydrazide,
N'-(4-hydroxybenzylidene)-2-naphthalenesulfonohydrazide,
N'-(1-phenylethylidene)-2-naphthalenesulfonohydrazide,
N'-diphenylmethylene-2-naphthalenesulfonohydrazide,
N'-(α-(2,4-dihydroxyphenyl)benzylidene)-2-naphthalenesulfonohydrazide,
N'-(2-furylmethylene)-2-naphthalenesulfonohydrazide,
N'-(1-methylethylidene)propanesulfonohydrazide,
N'-(1-methylpropylidene)propanesulfonohydrazide,
N'-(1,3-dimethylbutylidene)propanesulfonohydrazide,
N'-benzylidenepropanesulfonohydrazlde,
N'-(4-dimethylaminobenzylidene)propanesulfonohydrazide,
N'-(4-methoxybenzylidene)propanesulfonohydrazide,
N'-(2-hydroxybenzylidene)propanesulfonohydrazide,
N'-(4-hydroxybenzylidene)propanesulfonohydrazide,
N'-(1-phenylethylidene)propanesulfonohydrazide,
N'-diphenylmethylenepropanesulfonohydrazide,
N'-(α-(2,4-dihydroxyphenyl)benzylidene)propanesulfonohydrazide,
N'-(2-furylmethylene)propanesulfonohydrazide,
N'-(1-methylethylidene)isopropylsulfonohydrazide,
N'-(1-methylpropylidene)isopropylsulfonohydrazide,
N'-(1,3-dimethylbutylidene)isopropylsulfonohydrazide,
N'-benzylideneisopropylsulfonohydrazide,
N'-(4-dimethylaminobenzylidene)isopropylsulfonohydrazide,
N'-(4-methoxybenzylidene)isopropylsulfonohydrazide,
N'-(2-hydroxybenzylidene)isopropylsulfonohydrazide,
N'-(4-hydroxybenzylidene)isopropylsulfonohydrazide,
N'-(1-phenylethylidene)isopropylsulfonohydrazide,
N'-diphenylmethyleneisopropylsulfonohydrazide,
N'-(α-(2,4-dihydroxyphenyl)benzylidene)isopropylsulfonohydrazide,
N'-(2-furylmethylene)isopropylsulfonohydrazide,
N'-(1-methylethylidene)methanesulfonohydrazide,
N'-(1-methylpropylidene)methanesulfonohydrazide,
N'-(1,3-dimethylbutylidene)methanesulfonohydrazide,
N'-benzylidenemethanesulfonohydrazide,
N'-(4-dimethylaminobenzylidene)methanesulfonohydrazide,
N'-(4-methoxybenzylidene)methanesulfonohydrazide,
N'-(2-hydroxybenzylidene)methanesulfonohydrazide,
N'-(4-hydroxybenzylidene)methanesulfonohydrazide,
N'-(1-phenylethylidene)methanesulfonohydrazide,
N'-diphenylmethylenemethanesulfonohydrazide,
N'-(α-(2,4-dihydroxyphenyl)benzylidene)methanesulfonohydrazide,
N'-(2-furylmethylene)methanesulfonohydrazide,
N'-(1-methylethylidene)dodecanesulfonohydrazide,
N'-(1-methylpropylidene)dodecanesulfonohydrazide,
N'-(1,3-dimethylbutylidene)dodecanesulfonohydrazide,
N'-benzylidenedodecanesulfonohydrazide,
N'-(4-dimethylaminobenzylidene)dodecanesufonohydrazide,
N'-(4-methoxybenzylidene)dodecanesulfonohydrazide,
N'-(2-hydroxybenzylidene)dodecanesulfonohydrazide,
N'-(4-hydroxybenzylidene)dodecanesulfonohydrazide,
N'-(1-phenylethylidene)dodecanesulfonohydrazide,
N'-diphenylmethylenedodecanesulfonohydrazide,
N'-(α-(2,4-dihydroxyphenyl)benzylidene)dodecanesulfonohydrazide,
N'-(2-furylmethylene)dodecanesulfonohydrazide,
N'-(1-methylethylidene)-p-dodecylbenzenesulfonohydrazide,
N'-(1-methylpropylidene)-p-dodecylbenzenesulfonohydrazide,
N'-(1,3-dimethylbutylidene)-p-dodecylbenzenesulfonohydrazide,
N'-benzylidene-p-dodecylbenzenesulfonohydrazide,
N'-(4-dimethylaminobenzylidene)-p-dodecylbenzenesulfonohydrazide,
N'-(4-methoxybenzylidene)-p-dodecylbenzenesulfonohydrazide,
N'-(2-hydroxybenzylidene)-p-dodecylbenzenesulfonohydrazide,
N'-(4-hydroxybenzylidene)-p-dodecylbenzenesulfonohydrazide, N'-(1-phenylethylidene)-p-dodecylbenzenesulfonohydrazide,
N'-diphenylmethylene-p-dodecylbenzenesulfonohydrazide,
N'-(α-(2,4-dihydroxyphenyl)benzylidene)-p-dodecylbenzenesulfonohydrazide,
N'-(2-furylmethylene)-p-dodecylbenzenesulfonohydrazide,
N'-(1-methylethylidene)-4-acetamidobenzenesulfonohydrazide,
N'-(1-methylpropylidene)-4-acetamidobenzenesulfonohydrazide,
N'-(1,3-dimethylbutylidene)-4-acetamidobenzenesulfonohydrazide,
N'-benzylidene-4-acetamidobenzenesulfonohydrazide,
N'-(4-dimethylaminobenzylidene)-4-acetamidobenzenesulfonohydrazide,
N'-(4-methoxybenzylidene)-4-acetamidobenzenesulfonohydrazide,
N'-(2-hydroxybenzylidene)-4-acetamidobenzenesulfonohydrazide,
N'-(4-hydroxybenzylidene)-4-acetamidobenzenesulfonohydrazide,
N'-(1-phenylethylidene)-4-acetamidobenzenesulfonohydrazide,
N'-diphenylmethylene-4-acetamidobenzenesulfonohydrazide,
N'-(α-(2,4-dihydroxyphenyl)benzylidene)-4-acetamidobenzenesulfonohydrazide,
N'-(2-furylmethylene)-4-acetamidobenzenesulfonohydrazide, Among these various sulfonohydrazide compounds, preferred in terms of an aging-resistant effect, a raw material cost and ease in synthesis are N'-(1-methylethylidene) benzenesulfonohydrazide, N'-(1-methylpropylidene) benzenesulfonohydrazide, N'-(1,3-dimethylbutylidene) benzenesulfonohydrazide, N'-(1-phenylethylidene) benzenesulfonohydrazide, N'-(2-hydroxybenzylidene) benzenesulfonohydrazide, N'-diphenylmethylenebenzenesulfonohydrazide, N'-(2-furylmethylene)benzenesulfonohydrazide, N'-(1-methylethylidene)-p-toluenesulfonohydrazide, N'-(1-methylpropylidene)-p-toluenesulfonohydrazide, N'-(1,3-dimethylbutylidene)-p-toluenesulfonohydrazide, N'-benzylidene-p-toluenesulfonohydrazide, N'-(1-phenylethylidene)-p-toluenesulfonohydrazide, N'-(2-hydroxybenzylidene)-p-toluenesulfonohydrazide, N'-diphenylmethylene-p-toluenesulfonohydrazide and N'-(2-furylmethylene)-p-toluenesulfonohydrazide.

The sulfonohydrazide compounds represented by Formula (IV) described above are so good as to provide a hardening inhibition effect which has not been able to be achieved by conventional antioxidants and display particularly an excellent action against breaking properties after aging.

In the hardening inhibition effect described above, it is inferred that the specific sulfonohydrazide compounds described above selectively inhibit an increase in cross-linking which is particularly most related to hardening of rubber among various aging reactions.

These various sulfonohydrazide compounds can easily be synthesized by reacting compounds having hydrazide groups with prescribed ketone and aldehyde compounds or reacting hydrazide compounds with sulfonic acid chloride. The specific synthetic examples shall further be explained in the section of the examples.

The various hydrazide compounds represented by Formulas (I) to (IV) described above can be used alone or in combination of two or more kinds thereof. They are used in a range of 0.05 to 20 parts by weight, preferably 0.1 to 5.0 parts by weight per 100 parts by weight of the rubber component.

The amount of less than 0.05 part by weight of the aforementioned hydrazide compounds does not display the intended effect of the present invention, and the amount exceeding 20 parts by weight results in not only almost saturating the effect but also reducing the other physical properties and thus is not economical. Accordingly, both are not preferred.

The various hydrazide compounds represented by Formulas (I) to (IV) described above used in the present invention are effective as antioxidants even if they are used alone, but if they are used in combination with antioxidants usually used in the rubber industry, further higher aging-resistant effect can be obtained.

It has so far been known that when two or more kinds of antioxidants are used in combination, a synergetic effect is shown depending on the combination of the antioxidants used, and it is widely known that the kinds of these synergetic effects include homosynergism which takes place when two or more kinds of the antioxidants of a peroxy radical acceptor type are used in combination and heterosynergism which takes place when antioxidants having different action mechanisms are used in combination as is the case with, for example, the combination of the antioxidants of a peroxy radical acceptor type and the antioxidants of a peroxide decomposer type.

In the present invention, the various hydrazide compounds described above are the antioxidants of a peroxy radical acceptor type, and when they are used in combination with conventional other diphenylamine based and hindered phenol based antioxidants of a peroxy radical acceptor type, the former homosynergism is shown, and as a result, displayed is a specific effect such that the combined use of the hydrazide compounds provides more effect in a smaller amount than the single use of the existing diphenylamine based and hindered phenol based antioxidants does In a large amount.

If this hydrazide compound is compounded, the elastic modulus before and after degradation is less reduced than when a diphenyldiamine based antioxidant is compounded.

Antioxidants used in combination include, for example, naphthylamine base, p-phenylenediamine base, hydroquinone derivatives, bisphenol base, trisphenol base, polyphenol base, diphenylamine base, quinoline base, monophenol base, thiobisphenol base and hindered phenol base. Among them, amine based antioxidants of p-phenylenediamine base and diphenylamine base are preferred in terms of further higher aging-resistant effect.

The diphenylamine based antioxidants include, for example, 4,4'-(α-methylbenzyl)diphenylamine, 4,4'-(α,α-dimethylbenzyl)diphenylamine, p-(p-toluenesulfonylamido) diphenylamine and 4,4'-dioctyldiphenylamine. Among them, 4,4'-(α-methylbenzyl)diphenylamine is most preferred in terms of further higher aging-resistant effect.

The p-phenylenediamine based antioxidants include, for example, N,N'-diphenyl-p-phenylenediamine, N-isopropyl-N'-phenyl-p-phenylenediamine, N,N'-di-2-naphthyl-p-phenylenediamine, N-cyclohexyl-N'-phenyl-p-phenylenediamine, N-phenyl-N'-(3-methacryloyloxy-2-hydroxypropyl)-p-phenylenediamine, N,N'-bis(1- methylheptyl)-p-phenylenediamine, N,N'-bis(1,4-dimethylpentyl)-p-phenylenediamine, N,N'-bis(1-ethyl-3-methylpentyl)-p-phenylenediamine and N-(1,3-dimethylbutyl)-N'-phenyl-p-phenylenediamine. Among them, N-(1,3-dimethylbutyl)-N'-phenyl-p-phenylenediamine is most preferred in terms of further higher aging-resistant effect and a cost.

The antioxidants used in combination with the hydrazide compounds represented by Formulas (I) to (IV) described above can be used alone or in combination of two or more kinds thereof. They are used in a range of 0.1 to 5.0 parts by weight, preferably 0.2 to 4.0 parts by weight per 100 parts by weight of the rubber component.

The rubbers used in the present invention are natural and synthetic rubbers. The synthetic rubbers include, for example, cis-1,4-polyisoprene, styrene-butadiene copolymers, low cis-1,4-polybutadiene, high cis-1,4-polybutadiene, ethylene-propylene-diene copolymers, chloroprene rubber, halogenated butyl rubber and acrylonitrile-butadiene rubber, and at least one of them can be compounded. Preferred synthetic rubber is a diene based synthetic rubber.

Among these natural rubber and synthetic rubbers, natural rubber (which may be polyisoprene rubber) is used in a proportion of 30 phr, whereby a low heat generation property effect as well as an aging-resistant effect provided by the hydrazide compound can sufficiently be displayed.

Further, at least one of carbon black, silica, calcium carbonate and titanium oxide can be used as a reinforcing filler used in the present invention, and carbon black is preferred.

The compounding amount of the reinforcing filler is 20 to 150 parts by weight, preferably 25 to 80 parts by weight per 100 parts by weight of the rubber component described above. If the compounding amount of the reinforcing filler is less than 20 parts by weight, the breaking characteristic and the abrasion resistance of the vulcanized material are not sufficiently high, and the amount exceeding 150 parts by weight is not preferred in terms of the workability.

Carbon black used as the reinforcing filler includes, for example, carbon blacks such as HAF, ISAF and SAF.

The rubber composition blended with the hydrazide compounds represented by Formulas (I) to (IV) described above is used for a pneumatic tire to thereby obtain the pneumatic tire having an excellent aging-resistant characteristic.

Tire members for which the rubber composition is employed include tread, coating rubber for carcass or belt, side rubber, bead filler, rubber chafer and inliner.

In particular, the rubber composition blended with a part of the compounds described above among the hydrazide compounds represented by Formulas (I) or (II) has an excellent low heat generation property and is used for a tire tread part, whereby a pneumatic tire having an excellent low heat generation property can be obtained. In this case, preferred are carbon blacks having the characteristics of a specific surface area by nitrogen adsorption ($N_2SA$) of 30 to 180 $m^2$/g and a dibutyl phthalate absorption (DBP) of 60 to 200 ml/100 g, more preferably a specific surface area by nitrogen adsorption of 70 to 160 $m^2$/g and a DBP of 70 to 140 ml/100 g.

If carbon black has a $N_2SA$ of less than 30 and a DBP of less than 60, there is a small effect on improving the heat generation property. On the other hand, if the $N_2SA$ exceeds 180 and the DBP exceeds 200, the viscosity of non-vulcanized rubber rises to deteriorate the workability.

The compounding amount of carbon black having the characteristics described above is preferably 30 to 70 parts by weight, more preferably 35 to 60 parts by weight per 100 parts by weight of the rubber component described above.

In the present invention, the rubber composition can be blended, if necessary, with additives such as a vulcanizing agent, process oil, a vulcanization accelerator, zinc oxide (ZnO), stearic acid, an antioxidant, an antiozonant and a silane coupling agent each of which is usually used in the rubber industry as well as the rubber component, the reinforcing filler and the hydrazide compounds represented by Formulas (I) to (IV) described above.

The vulcanizing agent that can be used in the present invention includes, for example, sulfur and the like, and the using amount thereof is 0.1 to 10 parts by weight, preferably 0.5 to 5 parts by weight in terms of a sulfur content per 100 parts by weight of the rubber component. The amount of less than 0.1 part by weight tends to reduce the breaking characteristic and the abrasion resistance of the vulcanized rubber, and the amount exceeding 10 parts by weight tends to cause the rubber elasticity to be lost.

The process oil that can be used in the present invention includes, for example, paraffin base, naphthene base and aromatic base. The aromatic base is used for uses in which the breaking characteristic and the abrasion resistance are regarded as important, and the naphthene base or the paraffin base is used for uses in which the low heat generation property and the low temperature characteristic are regarded as important. The using amount thereof is 0 to 100 parts by weight per 100 parts by weight of the rubber material. The amount exceeding 100 parts by weight markedly degrades the breaking characteristic and the low heat generation property of the vulcanized rubber.

The vulcanization accelerators that can be used in the present invention shall not specifically be restricted and include preferably vulcanization accelerators of thiazole base such as 2-mercaptobenzothiazole (MBT) and dibenzothiazolyl disulfide (DM), sulfenamide base such as N-cyclohexyl-2-benzothiazolyl sulfenamide (CBS), N,N'-dicyclohexyl-2-benzothiazolyl sulfenamide and N-t-butyl-2-benzothiazolyl sulfenamide (BBS), and guanidine base such as diphenylguanidine (DPG). The using amount thereof is 0.1 to 5 parts by weight, preferably 0.2 to 3 parts by weight per 100 parts by weight of the rubber component.

The rubber composition of the present invention can be obtained by mixing the rubber component, the reinforcing filler, the compounds represented by Formulas (I) to (IV) described above and the like by means of a mixer such as a roll and an internal mixer. After the rubber composition is molded, it is vulcanized and can be used for industrial uses such as rubber vibration isolators, belts, hoses and other industrial articles as well as tire uses such as tire treads, under-treads, carcasses, side walls and bead parts. In particular, the rubber composition of the present invention is suitably used as rubber for tire tread.

EXAMPLES

The present invention shall be explained below in further detail with reference to synthetic examples, examples and comparative examples, but the present invention shall not be restricted to these examples.

Rubber compositions obtained in Examples and Comparative Examples were evaluated by the following testing methods to determine their characteristics.

(1) Mooney Scorch Test:

Carried out based on JIS K6300-1974. Measurement was conducted at 130° C. in the Mooney scorch test. MST (Mooney scorch time) in the Mooney scorch test is to evaluate liability to scorching of rubber at the time of molding rubber as in extruding and calendering, and the smaller the value is, the more the workability is degraded.

(2) Tensile Test:

The tensile test was carried out based on JIS K6301-1975 to determine an elongation at break (Eb), a tensile strength at break (Tb), a 100% modulus (M100) and a 300% modulus (M300).

(3) Hardness:

The hardness (Hd) was determined based on JIS K6301-1975.

(4) Air-heating Aging Test:

A sample was subjected to aging at a test temperature of 100±1° C. for 24 and 48 hours in a gear oven and then left standing at room temperature for 5 hours or longer. Subsequently, the tensile test described above was carried out in the same way as the case with the sample before aging.

All data were shown by index, wherein the measured value of a blank test (Comparative Example 1) in which no hydrazide compound was added was set at 100. The change rate was calculated from the following equation:

Measured Value after aging×100 Measured Value before aging (5) Evaluation of Heat Generation Property:

The heat generation property of the vulcanized rubber was evaluated by determining tan δ at 25° C. The tan δ (25° C.) was determined under the conditions of a dynamic distortion of 1% in stretching at a temperature of 25° C. and a frequency of 10 MHz by means of a mechanical spectrometer manufactured by Rheometrics Inc. U.S.

A reciprocal number of each tan δ obtained was shown by index to show the low heat generation property, wherein the value of a control (Comparative Example 3 in which no hydrazide compound was added) was set at 100.

It is meant that the larger the value of the low heat generation property index is, the larger the effect of low heat generation property by the hydrazide compounds is.

Synthetic Examples 1 to 13

Among the compounds represented by Formulas (I) and (II) in the present invention, $N^2,N^4$-di(1-methylethylidene)isophthalodihydrazide, N'-(1-methylethylidene)benzohydrazide, N'-diphenylmethylenebenzohydrazide, N'-(1,3-dimethylbutylidene)benzohydrazide, N'-(1,3-dimethylbutylidene)salicylohydrazide, N'-(2-furylmethylene)salicylohydrazide, 1-hydroxy-N'-(1,3-dimethylbutylidene)-2-naphthohydrazide, 3-hydroxy-N'-(1-methylethylidene)-2-naphthohydrazide, 3-hydroxy-N'-(1-methylpropylidene)-2-naphthohydrazide, 3-hydroxy-N'-(1,3-dimethylbutylidene)-2-naphthohydrazide, 3-hydroxy-N'-(1-furylmethylene)-2-naphthohydrazide, 3-hydroxy-N'-(2-furylmethylene)-2-naphthohydrazide and N'-(1-methylethylidene)isonicotinohydrazide which were the typical compounds were synthesized by the following methods:

Synthetic Example 1

Synthesis of $N^2,N^4$-di(1-methylethylidene) isophthalodihydrazide

A four neck flask (1 liter) equipped with a thermometer, a reflux condenser and a stirrer was charged with 58.2 g (0.3 mol) of isophthalohydrazide and 500 ml of acetone and then heated under reflux for 24 hours. The reaction liquid was cooled down to 20° C. or lower, and then crystal was filtered off and dried under reduced pressure, whereby the intended compound (white crystal) was obtained.

The amount yielded in this reaction was 81.2 g (0.23 mol), and the yield was 98%.

Melting point: 245° C.; $^1$H-NMR (DMSO) 1.93 (s, 6H), 1.99 (s, 6H), 7.60 to 8.30 (m, 4H), 10.54 (b, 2H).

The yield shows mol % (hereinafter the same shall apply regarding the yield).

Synthetic Example 2

Synthesis of N'-(1-methylethylidene) benzohydrazide

A four neck flask (1 liter) equipped with a thermometer, a reflux condenser and a stirrer was charged with 136 g (1.0 mol) of benzohydrazide and 600 ml of acetone and then heated under reflux for 12 hours. The reaction liquid was cooled down to 5° C. or lower, and then crystal was filtered off and dried under reduced pressure, whereby white crystal was obtained.

The amount yielded in this reaction was 148 g (0.84 mol), and the yield was 84%.

Melting point: 143° C.; $^1$H-NMR (DMSO) 1.92 (s, 3H), 1.98 (s, 3H), 7.40 to 7.95 (m, 5H), 10.42 (b, 1H).

Synthetic Example 3

Synthesis of N'-diphenylmethylenebenzohydrazide

A four neck flask (1 liter) equipped with a thermometer, a reflux condenser and a stirrer was charged with 68.0 g (0.5 mol) of benzohydrazide, 700 ml of methanol and 3.5 ml of acetic acid. Added thereto was 109.2 g (0.6 mol) of benzophenone while stirring at room temperature, and heating under reflux was continued for 12 hours. The reaction liquid was cooled down to 5° C. or lower, and then crystal was filtered off and dried under reduced pressure, whereby white crystal was obtained.

The amount yielded in this reaction was 103 g (0.34 mol), and the yield was 68%.

Melting point: 116° C.; $^1$H-NMR (DMSO) 7.30 to 7.70 (m, 15H), 10.05 (b, 1H).

Synthetic Example 4

Synthesis of N'-(1,3-dimethylbutylidene) benzohydrazide

A four neck flask (2 liters) equipped with a thermometer, a Dean-Stark type reflux condenser and a stirrer was charged with 68.0 g (0.5 mol) of benzohydrazide and 600 ml of methyl isobutyl ketone and then heated under reflux for 5 hours. The reaction liquid was cooled down to 5° C. or lower, and then crystal was filtered off and dried under reduced pressure, whereby white crystal was obtained.

The amount yielded in this reaction was 89.6 g (0.41 mol), and the yield was 82%.

Melting point: 110° C.; $^1$H-NMR (DMSO) 0.95,(m, 6H), 1.80 to 2.30 (m, 6H), 7.40 to 7.95 (m, 5H), 10.5 (b, 1H).

Synthetic Example 5

Synthesis of N'-(1,3-dimethylbutylidene) salicylohydrazide

A reactor equipped with a Dean-Stark type reflux condenser and a stirrer was charged with 1.7 liter of methyl isobutyl ketone and 190.2 g (1.25 mol) of salicylohydrazide and then heated under reflux for 5 hours while removing distilled water. The reaction liquid was cooled down to 20°

C., and then crystal deposited was filtered off and dried under reduced pressure, whereby white crystal was obtained.

The amount yielded in this reaction was 261 g, and the yield was 89%.

It was found from results of NMR and IR analyses that this substance was N'-(1,3-dimethylbutylidene) salicylohydrazide.

Melting point: 158° C.; $^1$H-NMR (DMSO) 0.90 (m, 6H), 1.89 (s, 3H), 1.97 (m, 1H), 2.15 (m, 2H), 6.95 (m, 2H), 7.35 (m, 1H), 7.93 (m, 1H), 11.00 (b, 1H), 11.75 (b, 1H); IR (KBr) 3400 to 2400, 1650, 1550, 1500, 1480, 1390, 1310, 1250, 1160, 1150, 1100, 1060, 910, 760, 660, 570, 540, 480 cm$^{-1}$.

Synthetic Example 6

Synthesis of N'-(2-furylmethylene)salicylohydrazide

A four neck flask (2 liters) equipped with a thermometer, a reflux condenser and a stirrer was charged with 76.1 g (0.5 mol) of salicylohydrazide and 1 liter of methanol, and 57.6 g (0.6 mol) of furfural was dropwise added thereto in 30 minutes while stirring at room temperature. After heating under reflux for 2 hours, the reaction liquid was cooled down to 20° C. or lower, and crystal was filtered off. The crystal was washed with a small amount of methanol and then dried under reduced pressure, whereby the intended compound (slightly yellow crystal) was obtained. The amount yielded in this reaction was 108.1 g (0.47 mol), and the yield was 93%.

Melting point: 211° C.; $^1$H-NMR (DMSO) 6.60 to 8.50 (m, 10H), 11.2 (b, 1H), 11.9 (b, 1H).

Synthetic Example 7

Synthesis of 1-hydroxy-N'-(1,3-dimethylbutylidene)-2-naphthohydrazide

A reactor equipped with a Dean-Stark type reflux condenser and a stirrer was charged with 500 ml of methyl isobutyl ketone and 50.0 g (0.25 mol) of 1-hydroxy-2-naphthohydrazide and then heated under reflux for 5 hours while removing distilled water. The reaction liquid was cooled down to 20° C., and then the solvent was distilled off by means of a rotary evaporator. Crystal was recrystallized from diethyl ether, whereby slightly yellow crystal was obtained.

The amount yielded in this reaction was 69.8 g, and the yield was 98%.

It was found from results of NMR and IR analyses that this substance was 1-hydroxy-N'-(1,3-dimethylbutylidene)-2-naphthohydrazide.

Melting point: 101° C.; $^1$H-NMR (DMSO) 0.90 (m, 6H), 2.00 (m, 4H), 2.23 (m, 2H), 7.93 (m, 1H), 7.56 (m, 2H), 7.88 (m, 2H), 8.25 (m, 1H), 10.87 (b, 1H), 14.15 (b, 1H); IR (KBr) 3400 to 2600, 1620, 1595, 1530, 1510, 1470, 1420, 1390, 1360, 1340, 1290, 1270, 1205, 1160, 1150, 820, 790, 760 cm$^{-1}$.

Synthetic Example 8

Synthesis of 3-hydroxy-N'-(1-methylethylidene)-2-naphthohydrazide

A four neck flask (3 liters) equipped with a thermometer, a reflux condenser and a stirrer was charged with 121.2 g (0.6 mol) of 3-hydroxy-2-naphthohydrazide, 1.14 g (0.006 mol) of p-toluenesulfonic acid and 2 liters of acetone and then heated under reflux for 5 hours. The reaction liquid was cooled down to 20° C. or lower, and then crystal was filtered off and dried under reduced pressure, whereby the intended compound (slightly yellow crystal) was obtained.

The amount yielded in this reaction was 130.5 g (0.54 mol), and the yield was 90%.

Melting point: 241° C.; $^1$H-NMR (DMSO) 1.96 (s, 3H), 2.03 (s, 3H), 7.32 (m, 2H), 7.50 (m, 1H), 7.75 (m, 1H), 7.95 (m, 1H), 8.57 (s, 1H), 11.2 (b, 1H), 11.62 (b, 1H).

Synthetic Example 9

Synthesis of 3-hydroxy-N'-(1-methylpropylidene)-2-naphthohydrazide

A four neck flask (3 liters) equipped with a thermometer, a reflux condenser and a stirrer was charged with 121.2 g (0.6 mol) of 3-hydroxy-2-naphthohydrazide and 2 liters of methyl ethyl ketone and then heated under refluxing for 5 hours. The reaction liquid was cooled down to 20° C. or lower, and then crystal was filtered off and dried under reduced pressure, whereby the intended compound (slightly yellow crystal) was obtained.

The amount yielded in this reaction was 135.1 g (0.53 mol), and the yield was 88%.

Melting point: 240° C.; $^1$H-NMR (DMSO) 0.92 to 1.15 (m, 3H), 1.90 to 2.05 (m, 3H), 2.25 to 2.42 (m, 2H), 7.75 to 8.60 (m, 6H), 11.00 to 11.30 (b, 2H).

Synthetic Example 10

Synthesis of 3-hydroxy-N'-(1,3-dimethylbutylidene)-2-naphthohydrazide

A reactor equipped with a Dean-Stark type reflux condenser and a stirrer was charged with 500 ml of methyl isobutyl ketone and 50.0 g (0.25 mol) of 3-hydroxy-2-naphthohydrazide and then heated under reflux for 5 hours while removing distilled water. The reaction liquid was cooled down to 20° C., and then crystal deposited was filtered off and dried under reduced pressure, whereby slightly yellow crystal was obtained.

The amount yielded in this reaction was 67.6 g, and the yield was 95%.

It was found from results of NMR and IR analyses that this substance was 3-hydroxy-N'-(1,3-dimethylbutylidene)-2-naphthohydrazide.

Melting point: 146° C.; $^1$H-NMR (DMSO) 0.90 (m, 6H), 1.93 (s, 3H), 2.00 (m, 1H), 2.17 (m, 2H), 7.38 (m, 2H), 7.46 (m, 1H), 7.75 (m, 1H), 7.95 (m, 1H), 8.58 (m, 1H), 11.15 (b, 1H), 11.65 (b, 1H); IR (KBr) 3400 to 2400, 1650, 1550, 1510, 1470, 1360, 1230, 1170, 1140, 1120, 1050, 950, 900, 880, 770, 740, 670, 600, 550, 480 cm$^{-1}$.

Synthetic Example 11

Synthesis of 3-hydroxy-N'-(1-phenylmethylene)-2-naphthohydrazide

A four neck flask (2 liters) equipped with a thermometer, a reflux condenser and a stirrer was charged with 101 g (0.5 mol) of 3-hydroxy-2-naphthohydrazide and 1.5 liter of methanol, and 63.7 g (0.6 mol) of benzaldehyde was dropwise added thereto in 30 minutes while stirring at room temperature. After heating under reflux for 5 hours, the reaction liquid was cooled down to 15° C. or lower, and crystal was filtered off. The crystal was washed with a small amount of methanol and then dried under reduced pressure, whereby the intended compound (slightly yellow crystal) was obtained.

The amount yielded in this reaction was 133.4 g (0.46 mol), and the yield was 92%.

Melting point: 232° C.; $^1$H-NMR (DMSO) 7.20 to 8.50 (m, 12H), 11.60 to 12.00 (b, 2H).

Synthetic Example 12

Synthesis of 3-hydroxy-N'-(2-furylmethylene)-2-naphthohydrazide

A four neck flask (2 liters) equipped with a thermometer, a reflux condenser and a stirrer was charged with 101 g (0.5 mol) of 3-hydroxy-2-naphthohydrazide and 1.5 liter of methanol, and 57.6 g (0.6 mol) of furfural was dropwise added thereto in 30 minutes while stirring at room temperature. After heating under reflux for 5 hours, the reaction liquid was cooled down to 20° C. or lower, and crystal was filtered off. The crystal was washed with a small amount of methanol and then dried under reduced pressure, whereby the intended compound (slightly yellow crystal) was obtained.

The amount yielded in this reaction was 118.6 g (0.42 mol), and the yield was 84%.

Melting point: 211° C.; $^1$H-NMR (DMSO) 6.60 to 8.50 (m, 10H), 11.2 (b, 1H), 11.9 (b, 1H).

Synthetic Example 13

Synthesis of N'-(1-methylethylidene) isonicotinohydrazide

A four neck flask (1 liter) equipped with a thermometer, a reflux condenser and a stirrer was charged with 68.5 g (0.5 mol) of isonicotinohydrazide and 500 ml of acetone and then heated under reflux for 24 hours. The reaction liquid was cooled down to 20° C. or lower, and then crystal was filtered off and dried under reduced pressure, whereby the intended compound (white crystal) was obtained.

The amount yielded in this reaction was 74.0 g (0.42 mol), and the yield was 84%.

Melting point: 162° C.; $^1$H-NMR (DMSO) 1.92 (s, 3H), 1.99 (s, 3H), 7.71 (m, 2H), 8.70 (m, 2H), 10.69 (b, 1H).

Examples 1 to 9 and Comparative Examples 1 to 2

Components shown in Table 1 and Table 2 were mixed and compounded by means of Labo Plastomill of 250 ml and a 3-inch roll.

Compounded rubbers (non-vulcanized) obtained in Examples 1 to 9 and Comparative Examples 1 to 2 were subjected to a Mooney scorch test. Further, these compounded rubbers were subjected to a tensile test and an air-heating aging test after vulcanization. These results are shown in the following Table 1 and Table 2.

TABLE 1

| Components | | Parts by weight |
| --- | --- | --- |
| Natural rubber | | 100 |
| Reinforcing filler | *1 | 40 |
| Stearic acid | | 2.5 |
| Antioxidant | *2 | 1.0 |
| Hydrazide compound | | Table 2 & Table 3 |
| ZnO | | 5.0 |
| CBS | *3 | 1.0 |
| Sulfur | | 2.0 |

*1: HAF grade carbon black
*2: Nocrac 6C (manufactured by Ohuchi Shinko Chemical Ind. Co., Ltd.) [N-(1,3-dimethylbutyl)-N'-phenyl-p-phenylenediamine]
*3: Nocceler CZ (manufactured by Ohuchi Shinko Chemical Ind. Co., Ltd.) [N-cyclohexyl-2-benzothiazolyl sulfenamide]

TABLE 2

| | | Comparative Example | | Example | | | |
| --- | --- | --- | --- | --- | --- | --- | --- |
| | | 1 Blank | 2 Chemical A | 1 Chemical B | 2 Chemical C | 3 Chemical D | 4 Chemical D |
| | Blending amount (part by weight) | | 1.0 | 1.0 | 1.0 | 1.0 | 0.5 |
| Mooney test (130° C.) | ML 1 + 4 | 100 | 124 | 103 | 98 | 98 | 98 |
| | MST | 100 | 25 | 55 | 67 | 83 | 91 |
| Tensile test | EB | 100 | 95 | 102 | 100 | 96 | 99 |
| | TB | 100 | 98 | 98 | 98 | 90 | 98 |
| | M300 | 100 | 103 | 93 | 100 | 87 | 98 |
| Tensile test after aging at 100° C. for 24 hours | EB | 100 | 102 | 106 | 105 | 104 | 102 |
| | TB | 100 | 103 | 101 | 101 | 101 | 102 |
| | M300 | 100 | 103 | 92 | 96 | 98 | 98 |
| Change rate (%) | EB | 80 | 85 | 83 | 84 | 88 | 83 |
| | TB | 93 | 97 | 85 | 95 | 104 | 96 |
| | M300 | 142 | 125 | 141 | 136 | 144 | 141 |
| Tensile test after aging at 100° C. for 48 hours | EB | 100 | 110 | 111 | 109 | 109 | 105 |
| | TB | 100 | 114 | 106 | 106 | 108 | 103 |
| | M300 | 100 | 105 | 92 | 98 | 97 | 98 |
| Change rate (%) | EB | 71 | 80 | 76 | 76 | 81 | 75 |
| | TB | 81 | 93 | 87 | 87 | 96 | 85 |
| | M300 | 152 | 147 | 150 | 149 | 152 | 151 |

TABLE 2-continued

|  |  | Example | | | | |
|---|---|---|---|---|---|---|
|  |  | 5<br>Chemical D | 6<br>Chemical D | 7<br>Chemical D | 8<br>Chemical E | 9<br>Chemical F |
|  | Blending amount<br>(part by weight) | 2.0 | 3.0 | 5.0 | 1.0 | 1.0 |
| Mooney test | ML 1 + 4 | 84 | 90 | 86 | 98 | 101 |
| (130° C.) | MST | 80 | 76 | 72 | 88 | 71 |
| Tensile test | EB | 101 | 102 | 104 | 103 | 102 |
|  | TB | 95 | 94 | 94 | 98 | 95 |
|  | M300 | 86 | 93 | 91 | 94 | 92 |
| Tensile test after | EB | 112 | 112 | 114 | 115 | 105 |
| aging at 100° C. | TB | 103 | 100 | 102 | 104 | 97 |
| for 24 hours | M300 | 98 | 95 | 91 | 89 | 92 |
| Change rate (%) | EB | 89 | 88 | 98 | 90 | 83 |
|  | TB | 100 | 99 | 100 | 98 | 95 |
|  | M300 | 145 | 145 | 143 | 134 | 142 |
| Tensile test after | EB | 120 | 124 | 122 | 114 | 111 |
| aging at 100° C. | TB | 114 | 111 | 109 | 107 | 101 |
| for 48 hours | M300 | 96 | 90 | 90 | 89 | 89 |
| Change rate (%) | EB | 84 | 86 | 83 | 78 | 77 |
|  | TB | 96 | 95 | 94 | 98 | 86 |
|  | M300 | 152 | 148 | 150 | 145 | 148 |

Chemicals A to F shown in Table 2 are as follows:

Chemical A: benzohydrazide

Chemical B: N'-(1-methylethylidene)benzohydrazide

Chemical C: N'-benzylidenebenzohydrazide

Chemical D: N'-diphenylmethylenebenzohydrazide

Chemical E: N'-(2-furylmethylidene)benzohydrazide

Chemical F: N'-diphenylmethylenepropionohydrazide

Comments on Table 2:

As apparent from the results shown in Table 2 described above, it has been confirmed that in Examples 1 to 19 falling in the scope of the present invention, the workability can be highly compatible with the rubber physical properties after aging as compared with Comparative Examples 1 to 2 falling outside the scope of the present invention.

To observe specifically, it can be found that in Comparative Example 2, an improving effect of EB and TB after aging is provided by benzohydrazide but MST is reduced to ¼ and the workability is deteriorated to a large extent.

In contrast with this, it can be found that in Examples 1 to 4 and 8 to 9, MST is prolonged to a large extent by turning benzohydrazide and propionohydrazide into hydrazones and that an improving effect of EB and TB after aging is almost maintained or elevated. Among them, N'-diphenylmethylenebenzohydrazide used in Examples 3 to 7 has a high aging-resistant effect and exerts a smaller influence on MST, and therefore the use of 0.5 part by weight or more thereof can allow the workability to be compatible with the after-aging breaking properties at a high level. Examples 10 to 28 and Comparative Examples 3 to 10 Components shown in Table 1 (some were changed in a rubber kind partially from natural rubber to synthetic rubber) and Table 3 were mixed and compounded by means of Labo Plastomill of 250 ml and a 3-inch roll. The respective compounded rubbers were vulcanized at 145° C. for 35 minutes and then subjected to measurement of a Mooney viscosity, a tensile test and an aging test. Further, the heat generation property was evaluated. These results are shown in Table 3.

TABLE 3

|  |  | Comparative Example | | | | | |
|---|---|---|---|---|---|---|---|
|  |  | 3<br>Blank | 4<br>Chemical G | 5<br>Chemical G | 6<br>Chemical G | 7<br>Chemical P | 8<br>Chemical R |
|  | Blending amount<br>(part by weight) |  | 0.5 | 1.0 | 1.5 | 1.0 | 1.0 |
|  | Kind of rubber | *1 | *1 | *1 | *1 | *1 | *1 |
| Mooney test | ML 1 + 4 | 42 | 47 | 50 | 56 | 65 | 45 |
| (130° C.) | MST | 16.0 | 13.0 | 9.8 | 6.1 | 13.0 | 7.8 |
| Tensile test | EB | 100 | 101 | 108 | 115 | 99 | 96 |
|  | TB | 100 | 99 | 100 | 102 | 98 | 99 |
|  | M300 | 100 | 98 | 95 | 93 | 101 | 95 |
| Tensile test after | EB | 100 | 107 | 122 | 131 | 102 | 97 |
| aging at 100° C. | TB | 100 | 104 | 110 | 113 | 99 | 97 |
| for 48 hours | M300 | 100 | 97 | 92 | 89 | 102 | 94 |
| Change rate (%) | EB | 71 | 75 | 80 | 81 | 73 | 72 |
|  | TB | 81 | 85 | 89 | 90 | 82 | 79 |
|  | M300 | 152 | 150 | 147 | 146 | 153 | 150 |
| Low heat build-up index |  | 100 | 137 | 144 | 152 | 155 | 132 |

TABLE 3-continued

|  |  | Example | | | | |
|---|---|---|---|---|---|---|
|  |  | 10<br>Chemical H | 11<br>Chemical H | 12<br>Chemical H | 13<br>Chemical H | 14<br>Chemical I |
|  | Blending amount<br>(part by weight) | 0.5 | 1.0 | 1.5 | 2.0 | 1.0 |
|  | Kind of rubber | *1 | *1 | *1 | *1 | *1 |
| Mooney test | ML 1 + 4 | 42 | 43 | 44 | 46 | 43 |
| (130° C.) | MST | 15.5 | 14.3 | 12.5 | 11.2 | 13.8 |
| Tensile test | EB | 102 | 104 | 110 | 118 | 105 |
|  | TB | 101 | 102 | 102 | 101 | 103 |
|  | M300 | 105 | 102 | 100 | 98 | 102 |
| Tensile test after | EB | 106 | 119 | 127 | 136 | 118 |
| aging at 100° C. | TB | 103 | 111 | 112 | 110 | 111 |
| for 48 hours | M300 | 102 | 98 | 95 | 93 | 100 |
| Change rate (%) | EB | 74 | 81 | 82 | 82 | 80 |
|  | TB | 83 | 88 | 89 | 88 | 87 |
|  | M300 | 148 | 146 | 144 | 144 | 149 |
| Low heat build-up index |  | 131 | 140 | 150 | 152 | 133 |

|  |  | Example | | | | |
|---|---|---|---|---|---|---|
|  |  | 15<br>Chemical J | 16<br>Chemical K | 17<br>Chemical K | 18<br>Chemical K | 19<br>Chemical K |
|  | Blending amount<br>(part by weight) | 1.0 | 0.5 | 1.0 | 1.5 | 2.0 |
|  | Kind of rubber | *1 | *1 | *1 | *1 | *1 |
| Mooney test | ML 1 + 4 | 44 | 43 | 43 | 44 | 44 |
| (130° C.) | MST | 14.2 | 15.8 | 14.9 | 13.8 | 12.4 |
| Tensile test | EB | 103 | 101 | 105 | 112 | 117 |
|  | TB | 102 | 104 | 104 | 103 | 102 |
|  | M300 | 103 | 107 | 104 | 103 | 101 |
| Tensile test after | EB | 119 | 107 | 117 | 129 | 133 |
| aging at 100° C. | TB | 108 | 108 | 108 | 108 | 106 |
| for 48 hours | M300 | 96 | 103 | 99 | 96 | 93 |
| Change rate (%) | EB | 82 | 75 | 79 | 82 | 81 |
|  | TB | 86 | 84 | 84 | 85 | 84 |
|  | M300 | 142 | 147 | 145 | 142 | 140 |
| Low heat build-up index |  | 131 | 130 | 142 | 152 | 153 |

|  |  | Example | | | | |
|---|---|---|---|---|---|---|
|  |  | 20<br>Chemical L | 21<br>Chemical M | 22<br>Chemical N | 23<br>Chemical O | 24<br>Chemical Q |
|  | Blending amount<br>(part by weight) | 1.0 | 1.0 | 1.0 | 1.0 | 1.0 |
|  | Kind of rubber | *1 | *1 | *1 | *1 | *1 |
| Mooney test | ML 1 + 4 | 42 | 44 | 42 | 41 | 55 |
| (130° C.) | MST | 15.1 | 14.5 | 14.6 | 13.1 | 14.2 |
| Tensile test | EB | 106 | 97 | 95 | 108 | 97 |
|  | TB | 105 | 103 | 104 | 101 | 96 |
|  | M300 | 105 | 111 | 112 | 103 | 104 |
| Tensile test after | EB | 121 | 107 | 106 | 123 | 101 |
| aging at 100° C. | TB | 110 | 109 | 110 | 108 | 98 |
| for 48 hours | M300 | 100 | 108 | 107 | 98 | 104 |
| Change rate (%) | EB | 81 | 78 | 79 | 81 | 74 |
|  | TB | 85 | 86 | 86 | 87 | 83 |
|  | M300 | 145 | 148 | 145 | 145 | 152 |
| Low heat build-up index |  | 127 | 135 | 141 | 145 | 146 |

TABLE 3-continued

|  |  | Example 25 Chemical S | *4 Comparative Example 9 Blank | *4 Example 26 Chemical K | *5 Comparative Example 10 Blank | *5 Example 27 Chemical K |
|---|---|---|---|---|---|---|
|  | Blending amount (part by weight) | 1.0 |  | 1.0 |  | 1.0 |
|  | Kind of rubber | *1 | *2 | *2 | *3 | *3 |
| Mooney test | ML 1 + 4 | 43 | 46 | 48 | 50 | 52 |
| (130° C.) | MST | 10.2 | 15.2 | 13.8 | 13.5 | 12.5 |
| Tensile test | EB | 103 | 100 | 105 | 100 | 102 |
|  | TB | 97 | 100 | 103 | 100 | 101 |
|  | M300 | 96 | 100 | 98 | 100 | 101 |
| Tensile test after | EB | 106 | 100 | 115 | 100 | 109 |
| aging at 100° C. | TB | 98 | 100 | 121 | 100 | 110 |
| for 48 hours | M300 | 95 | 100 | 100 | 100 | 108 |
| Change rate (%) | EB | 73 | 76 | 83 | 78 | 83 |
|  | TB | 82 | 80 | 94 | 88 | 96 |
|  | M300 | 151 | 123 | 126 | 150 | 160 |
| Low heat build-up index |  | 130 | 100 | 137 | 100 | 125 |

*1 Natural rubber 100 parts by weight
*2 Natural rubber 60 parts by weight
BR01 (manufactured by Japan Synthetic Rubber Co., Ltd.) 40 parts by weight
*3 Natural rubber 50 parts by weight
SBR01500 (manufactured by Japan Synthetic Rubber Co., Ltd.) 50 parts by weight
*4 The physical properties of Example 26 are shown by index, wherein those of Comparative Example 9 are set at 100.
*5 The physical properties of Example 27 are shown by index, wherein those of Comparative Example 10 are set at 100.

Chemicals G to S shown in Table 3 are as follows:
Chemical G: 3-hydroxy-2-naphthohydrazide
Chemical H: 3-hydroxy-N'-(1-methylethylidene)-2-naphthohydrazide
Chemical I: 3-hydroxy-N'-(1-methylpropylidene)-2-naphthohydrazide
Chemical J: 3-hydroxy-N'-(1-methylbutylidene)-2-naphthohydrazide
Chemical K: 3-hydroxy-N'-(1,3-dimethylbutylidene)-2-naphthohydrazide
Chemical L: 3-hydroxy-N'-(1-phenylethylidene)-2-naphthohydrazide
Chemical M: N'-(1-methylethylidene)salicylohydrazide
Chemical N: N'-(1,3-dimethylbutylidene)salicylohydrazide
Chemical O: 1-hydroxy-N'-(1,3-dimethylbutylidene)-2-naphthohydrazide
Chemical P: isophthalodihydrazide
Chemical Q: $N^2,N^4$-di(1-methylethylidene)isophthalodihydrazide
Chemical R: isonicotinohydrazide
Chemical S: N'-(1-methylethylidene)isonicotinohydrazide Comments on Table 3:

It can be found that as shown in Comparative Examples 3 to 8, conventional hydrazide compounds [Chemical G (3-hydroxy-2-naphthohydrazide), Chemical P (isophthalodihydrazide) and Chemical R (isonicotinohydrazide)] provide a high low heat generation property effect but cause a reduction in MST as well as a big rise in the Mooney viscosity.

In contrast with this, it has been confirmed that Chemical H [3-hydroxy-N'-(1-methylethylidene)-2-naphthohydrazide] is a little inferior in a low heat generation property in the same blending amount as compared with Chemical G but reduces the Mooney viscosity by 5 to 10 points and improves the workability to a large extent.

Further, as shown in Comparative Examples 4, 5 and 6, Examples 10, 11, 12 and 13 and Examples 16, 17, 18 and 19, an increase in the amounts of chemical H and Chemical K can achieve the low Mooney viscosity while lowering the heat generation property to the level that is equal to or less than Chemical G. It can also be found that the same effect can be obtained as well in Chemical I (Example 14), Chemical J (Example 15), Chemical L (Example 20), Chemical M (Example 21), Chemical N (Example 22) and Chemical O (Example 23).

Further, it has been confirmed that also when Chemical Q [$N^2,N^4$-di(1-methylethylidene)isophthalodihydrazide] and Chemical S [N'-(1-methylethylidene)isonicotinohydrazide] were used in place of Chemical P and Chemical R, the Mooney viscosity is reduced to a large extent while maintaining the same low heat generation property (Comparative Example 7 and Example 24 and Comparative Example 8 and Example 25).

Further, it has been confirmed that when the kind of rubber was changed and the case where Chemical K was used was compared with the case where no compound was added, the Mooney viscosity is reduced to a large extent while maintaining similarly the low heat generation property (Comparative Example 9 and Example 26 and Comparative Example 10 and Example 27).

Synthetic Examples 14 to 18

Among the compounds represented by Formula (III) in the present invention, five typical compounds of N-benzoyl-N'-phenylhydrazine, N-benzoyl-N'-salicyloylhydrazine, N-(3-hydroxy-2-naphthoyl)-N'-benzoylhydrazine, 1-benzamidoguanidine and 1-benzoylsemicarbazide were synthesized by the following methods:

Synthetic Example 14

Synthesis of N-benzoyl-N'-phenylhydrazine

A four neck flask (2 liters) equipped with a thermometer and a stirrer was charged with 216 g (2.0 mol) of phenyl-hydrazine and 1.5 liter of ether and cooled down to 5° C. Dropwise added thereto was 56.2 g (0.4 mol) of benzoyl chloride in 2 hours while stirring, and then the solution was heated to room temperature (20° C.) to continue stirring for 12 hours. Crystal was filtered off and washed sufficiently with deionized water and then dried under reduced pressure to obtain slightly brown crystal.

The amount yielded in this reaction was 61 g (0.29 mol), and the yield was 72%.

Melting point: 169° C.; $^1$H-NMR (DMSO) 6.66 to 7.95 (m, 11H), 10.36 (b, 1H).

Synthetic Example 15

Synthesis of N-benzoyl-N'-salicyloylhydrazine

A four neck flask (1 liter) equipped with a thermometer and a stirrer was charged with 60.8 g (0.4 mol) of salicylohydrazide, 49.2 g (0.6 mol) of sodium acetate and 700 ml of acetic acid. Dropwise added thereto was 67.4 g (0.48 mol) of benzoyl chloride in one hour while stirring, and stirring was continued at room temperature (20° C.) for 3 hours. After finishing the reaction, 1.5 liter of deionized water was added and crystal was filtered off. After washing sufficiently the crystal with 500 ml of methanol, it was dried under reduced pressure to obtain slightly brown crystal.

The amount yielded in this reaction was 96 g (0.37 mol), and the yield was 94%.

Melting point: 256° C.; $^1$H-NMR (DMSO) 6.80 to 8.00 (m, 9H), 10.65 (s, 2H), 11.92 (s, 1H).

Synthetic Example 16

Synthesis of N-(3-hydroxy-2-naphthoyl)-N'-benzoylhydrazine

A four neck flask (1 liter) equipped with a thermometer and a stirrer was charged with 60.6 g (0.3 mol) of 3-hydroxy-2-naphthohydrazide, 36.9 g (0.45 mol) of sodium acetate and 800 ml of acetic acid and heated to 30° C. Dropwise added thereto was 50.6 g (0.36 mol) of benzoyl chloride in one hour while stirring, and stirring was continued at 30° C. for one hour. After finishing the reaction, the reaction liquid was added to 1.5 liter of deionized water and crystal was filtered off. After washing sufficiently the crystal with 1 liter of deionized water and 500 ml of methanol, it was dried under reduced pressure to obtain slightly brown crystal.

The amount yielded in this reaction was 86 g (0.28 mol), and the yield was 93%.

Melting point: 256° C.; $^1$H-NMR (DMSO) 7.30 to 8.00 (m, 10H), 8.55 (s, 1H), 10.78 (b, 2H), 11.45 (b, 1H).

Synthetic Example 17

Synthesis of 1-benzamidoguanidine

A four neck flask (2 liters) equipped with a thermometer and a stirrer was charged with 88.5 g (1.0 mol) of aminoguanidine hydrochloride, 205 g (2.5 mol) of sodium acetate and 1 liter of acetic acid and cooled down to 10° C. Dropwise added thereto was 154.5 g (1.1 mol) of benzoyl chloride while stirring, and stirring was continued at room temperature (20° C.) for 12 hours. After filtering off crystal, the mother liquid was concentrated to obtain an oily substance. This was dissolved in 1 liter of deionized water, and a 48% sodium hydroxide aqueous solution was dropwise added until the pH became 13 or higher. Crystal deposited was filtered off and washed with 200 ml of deionized water, and then the crystal was dried under reduced pressure to obtain slightly brown crystal.

The amount yielded in this reaction was 111 g (0.73 mol), and the yield was 71%.

Melting point: 185° C.; $^1$H-NMR (DMSO) 6.80 to 7.20 (b, 4H), 7.25 (m, 3H), 7.90 (m, 2H), 10.80 (b, 1H).

Synthetic Example 18

Synthesis of 1-benzoylsemicarbazide

A four neck flask (1000 ml) equipped with a thermometer and a stirrer was charged with 78.2 g (0.75 mol) of 35% hydrochloric acid and 700 ml of deionized water. Added thereto was 68.0 g (0.5 mol) of benzohydrazide at room temperature (20° C.) while stirring, and then 60.7 g (0.75 mol) of potassium cyanate was gradually added in 30 minutes. Stirring was continued at 30° C. for one hour, and then crystal was filtered off and washed with 200 ml of deionized water. This was dried under reduced pressure to obtain white crystal.

The amount yielded in this reaction was 71.7 g (0.4 mol), and the yield was 80%.

Melting point: 220° C.; $^1$H-NMR (DMSO) 6.00 (b, 2H), 7.40 to 7.90 (m, 6H), 10.10 (b, 1H).

Examples 28 to 37 and Comparative Examples 11 to 14

Rubber compositions containing the components shown in the following Table 4 and Table 5 were mixed by means of a Banbury mixer and then molded to sheets (160 mm×160 mm) having a thickness of about 2 mm, followed by pressing cure at 145° C. for 30 minutes.

The vulcanized rubbers obtained in Examples 28 to 37 and Comparative Examples 11 to 14 were subjected to a tensile test before heat aging and after heat-aging in the air under the conditions of 100° C. and 48 hours to determine a 100% modulus and an elongation at break (%).

These results are shown in the following Table 5.

TABLE 2

| Components | | Parts by weight |
|---|---|---|
| Natural rubber | | 70 |
| Synthetic rubber | *1 | 30 |
| Reinforcing filler | *2 | 50 |
| Stearic acid | | 2.0 |
| Zinc oxide | | 3.0 |
| Antioxidant | *3 | Table 5 |
| Hydrazide compound | | Table 5 |
| Vulcanization accelerator | *4 | 1.0 |
| Sulfur | | 1.2 |

*1: JSR BR01 (manufactured by Japan Synthetic Rubber Co., Ltd.)
*2: ISAF grade carbon black
*3: Nocrac 6C (manufactured by Ohuchi Shinko Chemical Ind. Co., Ltd.) [N-(1,3-dimethylbutyl)-N'-phenyl-p-phenylenediamine]
*4: Nocceler CZ (manufactured by Ohuchi Shinko Chemical Ind. Co., Ltd.) [N-cyclohexyl-2-benzothiazolyl sulfenamide]

TABLE 5

| | | Blending amount (part by weight) | | Numeral in a parenthesis is a change rate before and after heat aging | | | |
|---|---|---|---|---|---|---|---|
| | | | | Before heat aging | | After heat aging | |
| | Hydrazide compound | Chemical F | Hydrazide compound | M100 | Elongation at break (Eb) (%) | M100 | Elongation at break (Eb) (%) |
| Comparative Example 11 | No addition | 0.00 | 0.00 | 1.71 | 545.2 | 2.13 (125) | 389.1 (71) |
| Example 28 | Chemical A | 0.00 | 1.00 | 2.25 | 535.1 | 3.05 (136) | 441.8 (83) |
| Example 29 | Chemical A | 0.00 | 2.00 | 2.37 | 532.4 | 3.11 (131) | 475.3 (89) |
| Comparative Example 12 | No addition | 1.00 | 0.00 | 2.11 | 527.2 | 3.13 (148) | 398.7 (76) |
| Comparative Example 13 | No addition | 2.00 | 0.00 | 2.45 | 520.0 | 4.41 (180) | 397.8 (77) |
| Comparative Example 14 | No addition | 5.00 | 0.00 | 1.90 | 578.8 | 3.99 (210) | 392.4 (68) |
| Example 30 | Chemical B | 1.00 | 1.00 | 1.87 | 538.9 | 2.58 (138) | 490.6 (91) |
| Example 31 | Chemical C | 1.00 | 1.00 | 2.03 | 531.2 | 2.71 (134) | 485.5 (91) |
| Example 32 | Chemical D | 1.00 | 1.00 | 2.74 | 521.1 | 3.50 (128) | 475.0 (91) |
| Example 33 | Chemical E | 1.00 | 1.00 | 2.54 | 526.5 | 3.17 (125) | 488.0 (93) |
| Example 34 | Chemical A | 1.00 | 1.00 | 2.61 | 526.0 | 3.19 (122) | 489.5 (93) |
| Example 35 | Chemical A | 1.00 | 2.00 | 2.65 | 525.2 | 3.18 (120) | 488.4 (93) |
| Example 36 | Chemical A | 1.00 | 3.00 | 2.71 | 520.3 | 3.22 (119) | 492.7 (95) |
| Example 37 | Chemical A | 1.00 | 0.50 | 2.37 | 531.0 | 3.13 (132) | 472.3 (89) |

Chemical A: N-benzoyl-N'-t-butylhydrazine
Chemical B: N-benzoyl-N'-phenylhydrazine
Chemical C: N,N'-dibenzoylhydrazine
Chemical D: 1-benzoylsemicarbazide
Chemical E: 1-benzamidoguanidine
Chemical F: N-(1,3-dimethylbutyl)-N'-phenyl-p-phenylenediamine Comments on Table 4 and Table 5:

As apparent from the results shown in Table 4 and Table 5, it has been confirmed that in Examples 28 to 37 falling in the scope of the present invention, 100% modulus after heat aging is excellent and an elongation at break is high as compared with those of Comparative Examples 11 to 14 falling outside the scope of the present invention.

It has been found that the rubber compositions having an excellent heat aging-resistant property can be obtained by using the aforementioned various hydrazide compounds of the present invention. Further, it has been found that the rubber compositions having further excellent heat aging-resistant property can be obtained by using the above hydrazide compounds in combination with the diphenyldiamine based antioxidants.

Synthetic Examples 19 to 24

Among the sulfonic acid hydrazone derivatives represented by Formula (IV) in the present invention, six tipical compounds of N'-(1-methylethylidene)benzenesulfonohydrazide, N'-benzylidenebenzenesulfonohydrazide, N'-(2-furylmethylene)benzenesulfonohydrazide, N'-diphenylmethylenebenzenesulfonohydrazide, N'-benzylidene-p-toluenesulfonohydrazide and N'-benzylidene-1-naphthalenesulfonohydrazide were synthesized by the following methods:

Synthetic Example 19

Synthesis of N'-(1-methylethylidene)benzenesulfonohydrazide

A four neck flask (1 liter) equipped with a thermometer, a reflux condenser and a stirrer was charged with 86 g (0.5 mol) of benzenesulfonohydrazide, 0.95 g (0.005 mol) of p-toluenesulfonic acid and 700 ml of acetone and then heated under reflux for about 5 hours. The reaction liquid was cooled down to 20° C. or lower, and then crystal was filtered off and dried under reduced pressure, whereby white crystal was obtained.

The amount yielded in this reaction was 97.5 g (0.46 mol), and the yield was 92%.

Melting point: 145° C.; $^1$H-NMR (DMSO) 1.77 (s, 6H), 7.50 to 7.90 (m, 5H), 10.05 (b, 1H).

Synthetic Example 20

Synthesis of N'-benzylidenebenzenesulfonohydrazide

A four neck flask (1 liter) equipped with a thermometer, a reflux condenser and a stirrer was charged with 86 g (0.5 mol) of benzenesulfonohydrazide and 700 ml of methanol, and 63.6 g (0.6 mol) of benzaldehyde was dropwise added thereto in one hour while stirring at room temperature and heated under reflux for about 5 hours. The reaction liquid was cooled down to 20° C. or lower, and then crystal was filtered off and dried under reduced pressure, whereby white crystal was obtained.

The amount yielded in this reaction was 115 g (0.445 mol), and the yield was 89%.

Melting point: 112° C.; $^1$H-NMR (DMSO) 7.20 to 8.40 (m, 12H).

Synthetic Example 21

Synthesis of N'-(2-furylmethylene) benzenesulfonohydrazide

A four neck flask (1 liter) equipped with a thermometer, a reflux condenser and a stirrer was charged with 86 g (0.5 mol) of benzenesulfonohydrazide and 700 ml of methanol, and 57.6 g (0.6 mol) of furfural was dropwise added thereto in one hour while stirring at room temperature and heated under reflux for about 5 hours. The reaction liquid was cooled down to 20° C. or lower, and then crystal was filtered off and dried under reduced pressure, whereby white crystal was obtained.

The amount yielded in this reaction was 94 g (0.37 mol), and the yield was 75%.

Melting point: 134° C.; $^1$H-NMR (DMSO) 6.52 (m, 1H), 6.80 (m, 1H), 7.50 to 7.90 (m, 7H), 11.51 (s, 1H).

Synthetic Example 22

Synthesis of N'-diphenylmethylenebenzenesulfonohydrazide

A four neck flask (2 liters) equipped with a thermometer, a reflux condenser and a stirrer was charged with 78.4 g (0.4 mol) of benzophenone hydrazone, 64.6 g (0.64 mol) of triethylamine and 1 liter of ether, and 105.6 g (0.6 mol) of benzenesulfonic acid chloride was dropwise added thereto in one hour while stirring at room temperature and then heated under reflux for 72 hours. The reaction liquid was cooled down to 20° C. and then washed (separated) twice with 500 ml of deionized water. The ether layer was dried over anhydrous magnesium sulfate and filtered off, and then the mother liquid was concentrated by means of a rotary evaporator to obtain reddish yellow crystal. This crude crystal was added to 1 liter of diethyl ether and heated under reflux for 30 minutes, and then the crystal was filtered off at 30° C. This was dried under reduced pressure to thereby obtain white crystal.

The amount yielded in this reaction was 94.1 g (0.28 mol), and the yield was 70%.

Melting point: 190° C.; $^1$H-NMR (DMSO) 7.10 to 8.00 (m, 15H), 10.52 (s, 1H).

Synthetic Example 23

Synthesis of N'-benzylidene-p-toluenesulfonohydrazide

A four neck flask (1 liter) equipped with a thermometer, a reflux condenser and a stirrer was charged with 93.0 g (0.5 mol) of p-toluenesulfonohydrazide and 700 ml of methanol, and 63.6 g (0.6 mol) of benzaldehyde was dropwise added thereto in one hour while stirring at room temperature and heated under reflux for about 5 hours. The reaction liquid was cooled down to 20° C. or lower, and then crystal was filtered off and dried under reduced pressure, whereby white crystal was obtained.

The amount yielded in this reaction was 123 g (0.45 mol), and the yield was 90%.

Melting point: 126° C.; $^1$H-NMR (DMSO) 2.35 (s, 3H), 7.20 to 7.80 (m, 10H), 10.10 (b, 1H).

Synthetic Example 24

Synthesis of N'-benzylidene-1-naphthalenesulfonohydrazide

A four neck flask (1 liter) equipped with a thermometer, a reflux condenser and a stirrer was charged with 111 g (0.5 mol) of 1-naphthalenesulfonohydrazide and 700 ml of methanol, and 63.6 g (0.6 mol) of benzaldehyde was dropwise added thereto in one hour while stirring at room temperature and heated under reflux for about 5 hours. The reaction liquid was cooled down to 20° C. or lower, and then crystal was filtered off and dried under reduced pressure, whereby white crystal was obtained.

The amount yielded in this reaction was 145 g (0.47 mol), and the yield was 94%.

Melting point: 153° C.; $^1$H-NMR (DMSO) 7.20 to 8.80 (m, 13H), 10.50 (b, 1H).

Examples 38 to 51 and Comparative Examples 15 to 16

Rubber compositions containing the components shown in the following Tables 6 to 7 and Tables 9 to 10 were mixed by means of a Banbury mixer and then molded to sheets (160 mm×160 mm) having a thickness of about 2 mm, followed by pressing cure at 145° C. for 30 minutes.

The vulcanized rubbers thus obtained were subjected to a hardness test and a tensile test before heat aging and after heat aging in the air at 100° C. for 48 hours to determine a hardness (Hd), a 300% modulus (M300), an elongation at break (Eb) and a tensile strength at break (Tb). The values thereof were shown by index, wherein the values of Comparative Examples 15 and 16 were set at 100.

These results are shown in the following Tables 8 and 11.

TABLE 6

| Components | | Parts by weight |
|---|---|---|
| Natural rubber | | 100 |
| Reinforcing filler | *1 | 50 |
| Stearic acid | | 2.0 |
| Zinc oxide | | 3.0 |
| Antioxidant | *2 | 1.0 |
| Sulfonic hydrazide | | Table 7 |
| Vulcanization accelerator | *3 | 0.8 |
| Sulfur | | 1.3 |

*1: HAF grade carbon black
*2: Nocrac 6C (manufactured by Ohuchi Shinko Chemical Ind. Co., Ltd.) [N-(1,3-dimethylbutyl)-N'-phenyl-p-phenylenediamine
*3: Nocceler NS-P (manufactured by Ohuchi Shinko Chemical Ind. Co., Ltd.) [N-tert-butyl-2-benzothiazolyl sulfenamide]

TABLE 7

| | Sulfonohydrazide | Blending amount (part by weight) |
|---|---|---|
| Comparative Example 15 | No addition | — |
| Example 38 | N'-diphenylmethylenebenzenesulfonohydrazide | 1.0 |
| Example 39 | N'-diphenylmethylenebenzenesulfonohydrazide | 2.0 |
| Example 40 | N'-diphenylmethylenebenzenesulfonohydrazide | 4.0 |
| Example 41 | N'-(1-methylethylidene)benzenesulfonohydrazide | 2.0 |
| Example 42 | N'-(1,3-dimethylbutylidene)benzenesulfonohydrazide | 2.0 |
| Example 43 | N'-(2-furylmethylidene)benzenesulfonohydrazide | 2.0 |
| Example 44 | N'-diphenylmethylene-p-toluenesulfonohydrazide | 2.0 |

TABLE 8

| | Before heat aging | | | | After heat aging | | | |
|---|---|---|---|---|---|---|---|---|
| | Hd | M300 | Eb | Tb | Hd | M300 | Eb | Tb |
| Comparative Example 15 | 100 | 100 | 100 | 100 | 100 (113.8) | 100 (160.6) | 100 (71.9) | 100 (78.9) |
| Example 38 | 101.7 | 101.2 | 100.9 | 100.3 | 97.0 (108.8) | 88.7 (140.7) | 103.4 (73.6) | 104.7 (82.4) |
| Example 39 | 103.4 | 102.8 | 102.4 | 101.0 | 95.5 (105.0) | 83.6 (130.5) | 113.8 (79.9) | 106.8 (83.5) |
| Example 40 | 105.2 | 103.8 | 103.1 | 101.0 | 95.5 (103.3) | 82.4 (127.5) | 115.4 (80.5) | 108.1 (84.5) |
| Example 41 | 101.7 | 100.7 | 100.6 | 100.1 | 95.5 (106.8) | 90.6 (144.6) | 103.7 (74.1) | 102.1 (80.6) |
| Example 42 | 101.7 | 102.2 | 101.3 | 100.6 | 95.5 (106.8) | 85.9 (135.0) | 109.8 (78.0) | 102.2 (80.2) |
| Example 43 | 103.4 | 103.2 | 101.6 | 99.6 | 95.5 (105.0) | 85.2 (132.7) | 110.6 (78.2) | 100.4 (79.5) |
| Example 44 | 101.7 | 101.0 | 100.8 | 100.4 | 95.5 (106.8) | 85.0 (135.1) | 103.8 (74.0) | 101.9 (80.1) |

Numeral in a parenthesis is a change rate before and after heat aging

TABLE 9

| Components | | Parts by weight |
|---|---|---|
| Synthetic rubber | *4 | 100 |
| Reinforcing filler | *5 | 60 |
| Stearic acid | | 2.0 |
| Aromatic oil | | 3.0 |
| Zinc oxide | | 3.0 |
| Antioxidant | *6 | 1.0 |
| Sulfonohydrazide | | Table 10 |
| Vulcanization accelerator 1 | *7 | 0.5 |
| Vulcanization accelerator 2 | *8 | 0.5 |
| Vulcanization accelerator 3 | *9 | 0.5 |
| Sulfur | | 1.3 |

*4: JSR 1502 (manufactured by Japan Synthetic Rubber Co., Ltd.)
5: HAF grade carbon black
6: Nocrac 6C (manufactured by Ohuchi Shinko Chemical Ind. Co., Ltd.) [N-(1,3-dimethylbutyl)-N'-phenyl-p-phenylenediamine
7: Nocceler NS-P (manufactured by Ohuchi Shinko Chemical Ind. Co., Ltd.) [N-tert-butyl-2-benzothiazolyl sulfenamide]
8: Nocceler DM-P (manufactured by Ohuchi Shinko Chemical Ind. Co., Ltd.) [dibenzothiazyl disulfide]
9: Nocceler D (manufactured by Ohuchi Shinko Chemical Ind. Co., Ltd.) [1,3-diphenylguanidine]

TABLE 10

| | Sulfonohydrazide | Blending amount (part by weight) |
|---|---|---|
| Comparative Example 16 | No addition | — |
| Example 45 | N'-diphenylmethylenebenzenesulfonohydrazide | 1.0 |
| Example 46 | N'-diphenylmethylenebenzenesulfonohydrazide | 2.0 |
| Example 47 | N'-diphenylmethylenebenzenesulfonohydrazide | 4.0 |

TABLE 10-continued

| | Sulfonohydrazide | Blending amount (part by weight) |
|---|---|---|
| Example 48 | N'-(1-methylethylidene)benzenesulfonohydrazide | 2.0 |
| Example 49 | N'-(1,3-dimethylbutylidene)benzenesulfonohydrazide | 2.0 |
| Example 50 | N'-(2-furylmethylidene)benzenesulfonohydrazide | 2.0 |
| Example 51 | N'-diphenylmethylene-p-toluenesulfonohydrazide | 2.0 |

TABLE 11

| | Before heat aging | | | | After heat aging | | | |
|---|---|---|---|---|---|---|---|---|
| | Hd | M300 | Eb | Tb | Hd | M300 | Eb | Tb |
| Comparative Example 16 | 100 | 100 | 100 | 100 | 100 (112.3) | 100 (157.1) | 100 (72.4) | 100 (81.9) |
| Example 45 | 101.8 | 100.8 | 100.3 | 100.2 | 98.4 (108.6) | 92.8 (144.7) | 105.5 (76.2) | 102.3 (83.6) |
| Example 46 | 103.5 | 102.3 | 101.1 | 100.5 | 96.9 (105.1) | 88.2 (135.5) | 112.3 (80.4) | 105.0 (85.6) |
| Example 47 | 105.3 | 102.8 | 101.4 | 100.7 | 96.9 (103.3) | 89.3 (136.5) | 113.1 (80.8) | 105.5 (85.7) |
| Example 48 | 101.8 | 100.3 | 100.2 | 100.3 | 98.4 (108.6) | 94.0 (147.2) | 106.0 (76.6) | 102.8 (83.9) |
| Example 49 | 101.8 | 101.7 | 100.7 | 100.0 | 96.9 (106.9) | 89.5 (138.3) | 109.1 (78.5) | 105.6 (86.5) |
| Example 50 | 103.5 | 102.8 | 100.3 | 99.7 | 96.9 (105.1) | 90.4 (138.1) | 108.3 (78.2) | 102.6 (84.2) |
| Example 51 | 101.8 | 100.2 | 100.7 | 99.8 | 96.9 (106.9) | 90.8 (142.4) | 107.4 (77.3) | 102.4 (84.0) |

Numeral in a parenthesis is a change rate before and after heat aging

Comments on Tables 8 and 11:

As apparent from the results shown in Tables 8 and 11, it has been confirmed that in Examples 38 to 51 falling in the scope of the present invention, a hardness (Hd) can be reduced even after heat aging and an elongation at break (Eb) and a tensile strength at break (Tb) are excellent as compared with those of Comparative Examples 15 to 16 falling outside the scope of the present invention.

Examples 52 to 60 and Comparative Examples 17 to 21

Rubber compositions were prepared in the compounding recipes shown in the following Table 12. Tires having a tire size of 3700R57 were produced to apply the respective rubber compositions shown in Table 12 to a tire rubber member (tread member) shown in FIG. 1. The hydrazide compounds A to J were compounded in the equimolar amounts respectively.

The respective experimental tires thus obtained were evaluated for a tire temperature, an abrasion resistance, a cut resistance and a workability by the following evaluation methods. The results thereof are shown in the following Table 12.

Evaluation of Tire Temperature:

A drum test was carried out at a fixed speed under a step road condition to measure a temperature in a position of a fixed depth of a tire tread and the results are shown by index, wherein the value of a control (Comparative Example 17 in which no hydrazide compound was added) was set at 100. The smaller the value of the index is, the larger the effect on low heat generation property is.

Evaluation of Abrasion Resistance:

The abrasion resistance was evaluated by calculating a value according to the following equation for the tread rubber of the tire after running for 2000 hours:

$$\text{travel distance}/(\text{groove depth before running} - \text{groove depth after running})$$

and showing the value by index, wherein the value of a control (Comparative Example 17) was set at 100. The larger the value of the index is, the larger the effect on improving the abrasion resistance is.

Evaluation of Cut Resistance:

The cut resistance (rupture resistance) was evaluated by determining an area rate per tread rubber surface 30 cm×30 cm in which the rubber does not peel off in the tire after running for 2000 hours and showing it by index, wherein the value of a control (Comparative Example 17) was set at 100. The larger the value of the index is, the larger the effect on improving the cut resistance is.

Evaluation of Workability:

The Mooney viscosity $ML_{1+4}$ (130° C.) was measured and shown by index, wherein the value of a control (Comparative Example 18 in which conventional 3-hydroxy-2-naphthohydrazide described in Japanese Pat. No. Laid-Open No. Hei 4-136048 was added) was set at 100. The larger the value of the index is, the larger the effect on improving the workability is.

TABLE 12

| | | Comparative Example | Example | | | | | | |
|---|---|---|---|---|---|---|---|---|---|
| | | 17 | 52 | 53 | 54 | 55 | 56 | 57 | 58 |
| Components | Natural rubber | 100 | 100 | 100 | 100 | 100 | 100 | 100 | 100 |
| | Carbon kind | A | A | A | A | A | A | A | A |
| | Black amount | 45 | 45 | 45 | 45 | 45 | 45 | 45 | 45 |
| | Stearic acid | 2 | 2 | 2 | 2 | 2 | 2 | 2 | 2 |
| | Paraffin wax | 2 | 2 | 2 | 2 | 2 | 2 | 2 | 2 |
| | Antioxidant*1 | 1 | 1 | 1 | 1 | 1 | 1 | 1 | 1 |
| | ZnO | 3 | 3 | 3 | 3 | 3 | 3 | 3 | 3 |
| | Vulcanization accelerator*2 | 1 | 1 | 1 | 1 | 1 | 1 | 1 | 1 |
| | Sulfur | 1.5 | 1.5 | 1.5 | 1.5 | 1.5 | 1.5 | 1.5 | 1.5 |
| | Hydrazide compound | — | A | B | C | D | E | F | G |
| | amount | — | 1.07 | 1.13 | 1.19 | 1.23 | 0.85 | 1.03 | 1.23 |
| Evaluation | Tire temperature | 100 | 83 | 85 | 88 | 80 | 83 | 82 | 78 |
| | Abrasion resistance | 100 | 102 | 103 | 102 | 100 | 99 | 100 | 99 |
| | Cut resistance | 100 | 101 | 105 | 101 | 102 | 100 | 100 | 100 |
| | Workability | 81 | 89 | 88 | 84 | 82 | 80 | 78 | 81 |

| | | Comparative Example | | | Example | Comparative Example | Example |
|---|---|---|---|---|---|---|---|
| | | 18 | 19 | 20 | 59 | 21 | 60 |
| Components | Natural rubber | 100 | 100 | 100 | 100 | 100 | NR/SBR 70/30 |
| | Carbon kind | A | A | A | A | A | A |
| | Black amount | 45 | 45 | 40 | 45 | 75 | 45 |
| | Stearic acid | 2 | 2 | 2 | 2 | 2 | 2 |
| | Paraffin wax | 2 | 2 | 2 | 2 | 2 | 2 |
| | Antioxidant*1 | 1 | 1 | 1 | 1 | 1 | 1 |
| | ZnO | 3 | 3 | 3 | 3 | 3 | 3 |
| | Vulcanization Accelerator*2 | 1 | 1 | 1 | 1 | 1 | 1 |
| | Sulfur | 1.5 | 1.5 | 1.5 | 1.5 | 1.5 | 1.5 |
| | Hydrazide compound | I | J | — | H | A | A |
| | amount | 1.0 | 1.0 | — | 1.1 | 1.07 | 1.07 |
| Evaluation | Tire temperature | 88 | 81 | 88 | 80 | 115 | 89 |
| | Abrasion resistance | 100 | 100 | 83 | 100 | 110 | 109 |
| | Cut resistance | 101 | 99 | 81 | 100 | 125 | 120 |
| | Workability | 100 | 135 | 75 | 100 | 130 | 91 |

Kind of carbon black: A: N220 ($N_2SA$ = 120, DBP = 119)
*1 Santflex 13 (N-(1,3-dimethyl)-N'-phenyl-phenylenediamine)
*2 N-tert-butyl-2-benzothiazole sulfenamide In Table 12, the hydrazide compounds A to J represent the following compounds:

A: 3-hydroxy-N'-(1-methylethylidene)-2-naphthohydrazide
B: 3-hydroxy-N'-(1-methylpropylidene)-2-naphthohydrazide
C: 3-hydroxy-N'-(1-methylbutylidene)-2-naphthohydrazide
D: 3-hydroxy-N'-(1,3-dimethylbutylidene)-2-naphthohydrazide
E: N'-(1-methylethylidene)salicylohydrazide
F: N'-(1,3-dimethylbutylidene)salicylohydrazide
G: 1-hydroxy-N'-(1,3-dimethylbutylidene)-2-naphthohydrazide
H: $N^2,N^4$-di(1-methylethylidene)isophthalodihydrazide
I: 3-hydroxy-2-naphthohydrazide
J: isophthalodihydrazide Comments on Table 12:

As apparent from the results shown in Table 12, it has been confirmed that Examples 52 to 60 falling in the scope of the present invention are improved in workability to a large extent while keeping a tire temperature, an abrasion resistance and a cut resistance equal or higher as compared with those of Comparative Examples 17 to 21 falling outside the scope of the present invention.

To observe the individual cases, no heat generation property-improving agent was added in Comparative Example 17 (control), and it can be found in this case that the workability is extremely degraded. In Comparative Example 18, 3-hydroxy-2-naphthohydrazide described in Japanese Pat. No. Laid-Open No. Hei 4-136048 which was a conventional technique was added and in Comparative Example 19, isophthalodihydrazide was added. It can be found that the low heat generation property is achieved but the workability is extremely deteriorated. In Comparative Example 20, the amount of carbon black is reduced by 5 weight parts compared with Comparative Example 17, and it can be found in this case that balance among the workability, the abrasion resistance and the cut resistance is not improved. In Comparative Example 21, 3-hydroxy-N'-(1-methylethylidene)-2-naphthohydrazide which is the chemical substance of the present invention is used. However, carbon black is used in a large amount, and therefore it can be found that the tire temperature is elevated though the abrasion resistance and the cut resistance are improved, and that the workability is deteriorated as well to a large extent.

In contrast with this, it has been confirmed that in any of Examples 52 to 60 each of which falls in the scope of the present invention, the workability is improved to a large extent while keeping the tire temperature, the abrasion resistance and the cut resistance equal or higher.

Industrial Applicability

The rubber composition of the present invention can be used for industrial articles such as rubber vibration isolators, belts and hoses as well as tire materials such as tire treads, undertreads, carcasses, side walls and beads. In particular, the use thereof for a tire tread can provide a tire having a low heat generation property.

What is claimed is:

1. A rubber composition prepared by compounding 0.05 to 20 parts by weight of at least one hydrazide compound selected from the group consisting of hydrazide compounds represented by the following Formula (II) per 100 parts by weight of a rubber component comprising at least one rubber selected from the group consisting of natural rubber and synthetic rubber:

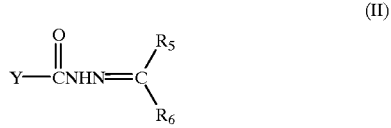

wherein Y represents a naphthyl group which may be substituted with at least one substituent containing at least one atom of carbon, sulfur, oxygen and nitrogen atoms; $R_5$ and $R_6$ each represent hydrogen, an alkyl group having 1 to 18 carbon atoms, a cycloalkyl group, an alkenyl group or an aromatic group which may be substituted with at least one substituent containing at least one atom of carbon, sulfur, oxygen and nitrogen atoms, and each of $R_5$ and $R_6$ may be the same or different, and when $R_5$ and $R_6$ are alkyl groups, $R_5$ may be bonded to $R_6$ to form a ring.

2. The rubber composition as described in claim 1, containing 30 phr or more of natural rubber or polyisoprene rubber as the rubber component.

3. The rubber composition as described in claim 1 prepared by further compounding 20 to 150 parts by weight of a reinforcing filler.

4. The rubber composition as described in claim 3, wherein the reinforcing filler is carbon black.

5. The rubber composition as described in claim 1, wherein the hydrazide compound represented by Formula (II) is 1-hydroxy-N'-(1-methylethylidene)-2-naphthohydrazide,
1-hydroxy-N'-(1-methylpropylidene)-2-naphthohydrazide,
1-hydroxy-N'-(1,3-dimethylbutylidene)-2-naphthohydrazide,
1-hydroxy-N'-(2-furylmethylene)-2-naphthohydrazide,
3-hydroxy-N'-(1-methylethylidene)-2-naphthohydrazide,
3-hydroxy-N'-(1-methylpropylidene)-2-naphthohydrazide,
3-hydroxy-N'-(1,3-dimethylbutylidene)-2-naphthohydrazide or
3-hydroxy-N'-(2-furylmethylene)-2-naphthohydrazide.

6. The rubber composition as described in any of claim 1, prepared by further compounding 0.1 to 5.0 parts by weight of at least one antioxidant selected from the group consisting of antioxidants of naphthylamine base, p-phenylenediamine base, hydroquinone derivative, bisphenol base, trisphenol base, polyphenol base, diphenylamine base, quinoline base, thiobisphenol base and hindered phenol base.

7. A pneumatic tire comprising a rubber composition prepared by compounding 0.05 to 5 parts by weight of at least one hydrazide compound selected from the group consisting of the hydrazide compounds represented by Formula (II) per 100 parts by weight of a rubber component comprising at least one rubber selected from the group consisting of natural rubber and synthetic rubber:

wherein Y represents a naphthyl group which may be substituted with at least one substituent containing at least one atom of carbon, sulfur, oxygen and nitrogen atoms; $R_5$ and $R_6$ each represent hydrogen, an alkyl group having 1 to 18 carbon atoms, a cycloalkyl group, an alkenyl group or an aromatic group which may be substituted with at least one substituent containing at least one atom of carbon, sulfur, oxygen and nitrogen atoms, and each of $R_5$ and $R_6$ may be the same or different, and when $R_5$ and $R_6$ are alkyl groups, $R_5$ may be bonded to $R_6$ to form a ring.

8. The pneumatic tire as described in claim 7, wherein the tire comprises a tread part which comprises said rubber composition.

9. The pneumatic tire as described in claim 8, wherein the hydrazide compound represented by Formula (II) is 1-hydroxy-N'-(1-methylethylidene)-2-naphthohydrazide,
1-hydroxy-N'-(1-methylpropylidene)-2-naphthohydrazide,
1-hydroxy-N'-(1,3-dimethylbutylidene)-2-naphthohydrazide,
1-hydroxy-N'-(2-furylmethylene)-2-naphthohydrazide,
3-hydroxy-N'-(1-methylethylidene)-2-naphthohydrazide,
3-hydroxy-N'-(1-methylpropylidene)-2-naphthohydrazide,
3-hydroxy-N'-(1,3-dimethylbutylidene)-2-naphthohydrazide or
3-hydroxy-N'-(2-furylmethylene)-2-naphthohydrazide.

10. The pneumatic tire as described in claim 8, wherein the rubber composition constituting the tread further comprises 30 to 70 parts by weight of carbon black having a specific surface area by nitrogen adsorption ($N_2SA$) of 30 to 180 $m^2/g$ and a dibutyl phthalate absorption (DBP) of 60 to 200 ml/100 g compounded per 100 parts by weight of the rubber component comprising at least one rubber selected from the group consisting of natural rubber and synthetic rubber; and Y in Formula (II) is a naphthyl group substituted with a hydroxyl group or an amino group.

11. A hydrazone derivative represented by Formula (V):

wherein Z represents a 3-hydroxy-2-naphthyl or a 1-hydroxy-2-naphthyl group.

* * * * *